(12) United States Patent
Reiner

(10) Patent No.: US 8,655,677 B2
(45) Date of Patent: Feb. 18, 2014

(54) PRODUCTIVITY WORKFLOW INDEX

(76) Inventor: Bruce Reiner, Berlin, MD (US)

( * ) Notice: Subject to any disclaimer, the term of this patent is extended or adjusted under 35 U.S.C. 154(b) by 947 days.

(21) Appl. No.: 12/137,926

(22) Filed: Jun. 12, 2008

(65) Prior Publication Data

US 2008/0312963 A1 Dec. 18, 2008

Related U.S. Application Data

(60) Provisional application No. 60/929,081, filed on Jun. 12, 2007.

(51) Int. Cl.
*G06Q 10/00* (2012.01)
*G06Q 50/00* (2012.01)
(52) U.S. Cl.
USPC .................................................. 705/2; 705/3
(58) Field of Classification Search
USPC ....................................................... 705/2–4
See application file for complete search history.

(56) References Cited

U.S. PATENT DOCUMENTS

| | | | |
|---|---|---|---|
| 7,349,859 B1 | 3/2008 | Lamer et al. | |
| 7,421,647 B2 | 9/2008 | Reiner | |
| 2003/0212580 A1* | 11/2003 | Shen | 705/2 |
| 2003/0220815 A1* | 11/2003 | Chang et al. | 705/2 |
| 2004/0220836 A1* | 11/2004 | Doherty et al. | 705/3 |
| 2005/0033594 A1* | 2/2005 | Shen | 705/1 |
| 2007/0046649 A1 | 3/2007 | Reiner | |
| 2007/0106633 A1 | 5/2007 | Reiner | |
| 2007/0118401 A1 | 5/2007 | Mahesh et al. | |
| 2007/0233520 A1* | 10/2007 | Wehba et al. | 705/3 |
| 2007/0239376 A1 | 10/2007 | Reiner | |

* cited by examiner

*Primary Examiner* — Michelle L Le
(74) *Attorney, Agent, or Firm* — Jean C. Edwards, Esq.; Edwards Neils PLLC

(57) ABSTRACT

Provided are methods of providing productivity measure for a complex workflow process, be determining at least one Productivity Workflow Index (PWI) based on data regarding human computer actions and workflow-related variables. Also provided are systems, apparatuses, machine-readable medium, and computer readable program products relating to such methods.

20 Claims, 5 Drawing Sheets

PRODUCTIVITY WORKFLOW INDEX

RELATED APPLICATION

This patent application claims the benefit of priority to U.S. Provisional Patent Application No. 60/929,081 filed on Jun. 12, 2007. The provisional patent application is hereby incorporated by reference in its entirety.

FIELD

Example embodiments are generally directed to methods for providing productivity measures for a complex workflow process, particularly in the medical field. Example embodiments are generally directed to computer-implemented methods of determining productivity in medical workflow processes, which include determining at least one Productivity Workflow Index (PWI) based on data regarding human computer actions and workflow-related variables. Such methods may include the actual recording of such data and/or may include accessing such data from one or more databases, and using the data to determine at least one individual and/or pooled PWI score.

In determining a PWI score, various methods may be employed, such as weighting individual data elements, and assigning a PWI score based on a sum of the weighted data, to provide measures of productivity based on various factors in specific workflow scenarios.

According to non-limiting example embodiments, data may be pooled to provide various peer PWI scores against which PWI scores of an individual, facility, type of profession, etc. may be compared.

According to other non-limiting example embodiments, individual and/or pooled data or PWI scores may be used to determine improved workflow processes, determine compensation, medical malpractice rates, and the like.

Also encompassed are systems, apparatuses, machine-readable medium, and computer-readable program products relating to methods provided herein.

BACKGROUND

Productivity measures are typically comprised of single variables that do not take into account the multitude of individual metrics that constitute a complex workflow process. In the case of medicine for example, a physician, technologist, administrator or information technology (IT) specialist must go through multiple individual steps to complete a process. For physicians, these multi-step processes can include interpretation of a medical imaging exam (radiologist), performance of medical consultation (internist), admitting history and physical (hospitalist), or complex surgical procedure (surgeon). Regardless of the specific process or job description, the workflow processes performed are far too complex to measure in beginning and end times alone.

For years, a metric termed the relative value unit (RVU) was used as the primary measurement tool to predict the time and effort required within medical imaging to complete the performance and interpretation of a medical imaging exam. This Productivity metric was in turn tied to economic reimbursement, with the general idea that RVU's were directly proportional to the time and effort spent in performing the procedure and as a result should correlate with the economic payment. A number of problems existed with this system, most notably the fact that RVU's were calculated long ago before the development of current technologies (imaging and information system technologies), RVU's were not directly tied to quality measures, and RVU's did not take into account variability (between practitioners) of data being analyzed and workflow differences. As a result, two individuals performing the same function (e.g. interpretation of a chest CT (computed tomography)) were reimbursed in an identical fashion, regardless of significant differences in the technology used, number and type of data being reviewed and analyzed, and overall accuracy of the interpretations.

To illustrate how present productivity and quality may vary, a few Comparative Examples are provided in the Examples section below.

SUMMARY

As described further herein, the methods developed by the present inventor, provide more accurate and reliable productivity measurement tools for complex workflow processes, particularly in the medical field. The present methods may take into account the multitude of variables that account for overall level of difficulty including (but not limited to) patient profile and clinical profile, technologies utilized, complexity and quantity of data being analyzed, as well as technical difficulty (for example, for an interventional or surgical procedure). Such methods may provide not only a measure for reviews and/or compensation determinations of medical professionals and facilities, but also provide measures that enable institutions and individuals to modify their workflow to increase productivity, efficiency, and ultimately obtain better overall patient outcomes.

Example embodiments are generally directed to computer-implemented methods of determining productivity in medical workflow processes, which include determining at least one Productivity Workflow Index (PWI) based on data regarding human computer actions and workflow-related variables. Such methods may include for example, methods that include recording data regarding human computer actions and workflow related variables; recording data regarding the human computer actions and the workflow related variables to an electronic database; repeating the recording steps multiple times for the first user or a second or more users, relating to a second or more patients; pooling the data; and determining at least one Productivity Workflow Index from the pooled data.

Other example methods may include determining at least one Productivity Workflow Index using data regarding human computer actions and workflow-related variables, where the data was obtained from other sources that have been recorded on at least one accessible database. For example, such methods may include pooling data regarding human computer actions by a user and workflow-related variables from an electronic database; and determining at least one Productivity Workflow Index from the pooled data. PWI scores may be determined for example, by assigning weighted values to particular data.

In embodiments that include recording the data, the recording may include not only recording that a user performed certain activities (e.g., that certain information or databases were accessed by the user, or certain reports generated), but also may include time-stamping the human computer actions, so data is available regarding the time spent performing each activity.

Workflow-related variables according to example embodiments may include at least one variable selected from the group consisting of patient profile, institutional profile, technology profile, clinical profile, imaging profile, exam profile, and outcomes profile.

A Productivity Workflow Index (PWI) may be determined from a pooled set of data and/or from calculated individual PWI scores. PWI scores may be determined by a variety of methods. An example of such a method may include using for example, a weighting system, where certain individual data elements, such as certain actions and variables, may be assigned a particular numerical value. The time spent on each activity may also play a role in determining a PWI score.

Example methods provided herein may include determining a Productivity Workflow Index (PWI) for a single user, using data regarding that user's human computer actions and workflow-related variables. The PWI for a single user may be calculated, for example, by assigning weighted values to data regarding that user's human computer actions and workflow related variables. The PWI for a single user may be calculated based on actions and variables related to a single patient, or based on actions related to multiple patients (for example, regarding all of that user's actions with respect to patients having had chest CTs, or for example, regarding all of that user's actions in a particular year, or all of that user's actions overall).

Moreover, methods described herein that include pooling data to determine a pooled Productivity Workflow Index may further include determining a Productivity Workflow Index for a single user (for example by assigning weighted values to data regarding that user's human computer actions and workflow-related variables); and comparing the Productivity Workflow Index for the single user, to at least one Productivity Workflow Index calculated from the pooled data.

Methods described herein that include pooling data to determine a pooled Productivity Workflow Index may further include determining a Productivity Workflow Index for a first pooled group of users and patients based on human computer actions and workflow-related variables within the pooled group; and comparing the Productivity Workflow Index for the first pooled group, to at least one Productivity Workflow Index from a second pooled group of users and patients.

Also provided are computer-implemented methods for providing an estimated completion time for a workflow process in the medical field, which include determining at least one estimated Productivity Workflow Index for a workflow process by assigning weighted values to recorded data regarding human computer actions and workflow-related variables, where the Productivity Workflow Index includes information regarding an estimated completion time for a workflow process or portions thereof; and displaying estimated completion time information to the user performing the workflow process. The estimated completion time may be for example, time until overall completion of the workflow process, completion of a portion of the workflow, running clock information, and countdown clock information.

Example embodiments are also directed to apparatuses that include a server and software capable of performing methods herein or portions thereof. By way of non-limiting example, software may be capable of determining various pooled and/or individual PWI scores, and optionally comparing such scores.

Example embodiments also include systems that include a server coupled to a database. The database may be one or more databases that include information regarding recorded human computer actions by at least one user and at least one patient and information regarding workflow-related variables. The server may include software capable of performing the methods herein, or a portion of such methods. By way of non-limiting example, software may be capable of determining various pooled and/or individual PWI scores, and optionally comparing such scores.

Example embodiments are also generally directed to a machine readable medium (such as a computer readable medium) that include code segments embodied on a medium that, when read by a machine, cause the machine to perform any of the present methods or portions thereof. Thus, example embodiments of a machine readable medium may include executable instructions to cause a device to perform one or more of the present methods or portions thereof.

Example embodiments also include computer-readable program products that include a computer-readable medium and a program for performing one or more of the present methods or portions thereof.

There has thus been outlined, some features that are consistent with the present inventions in order that the detailed description thereof that follows may be better understood, and in order that the present contributions to the art may be better appreciated. There are, of course, additional features consistent with the present invention that will be described below and which will form the subject matter of the claims appended hereto.

In this respect, before explaining embodiments in detail, it is to be understood that the embodiments described herein are not limited in their application to the details of construction and to the arrangements of the components set forth in the following description or illustrated in the drawings. Methods, systems, apparatuses' and the like consistent with the present invention are capable of other embodiments and of being practiced and carried out in various ways. Also, it is to be understood that the phraseology and terminology employed herein, as well as the abstract included below, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the methods and apparatuses consistent with the present invention.

BRIEF DESCRIPTION OF THE DRAWINGS

Embodiments are herein described, by way of non-limiting example, with reference to the following accompanying drawings.

DETAILED DESCRIPTION

Figure 1:
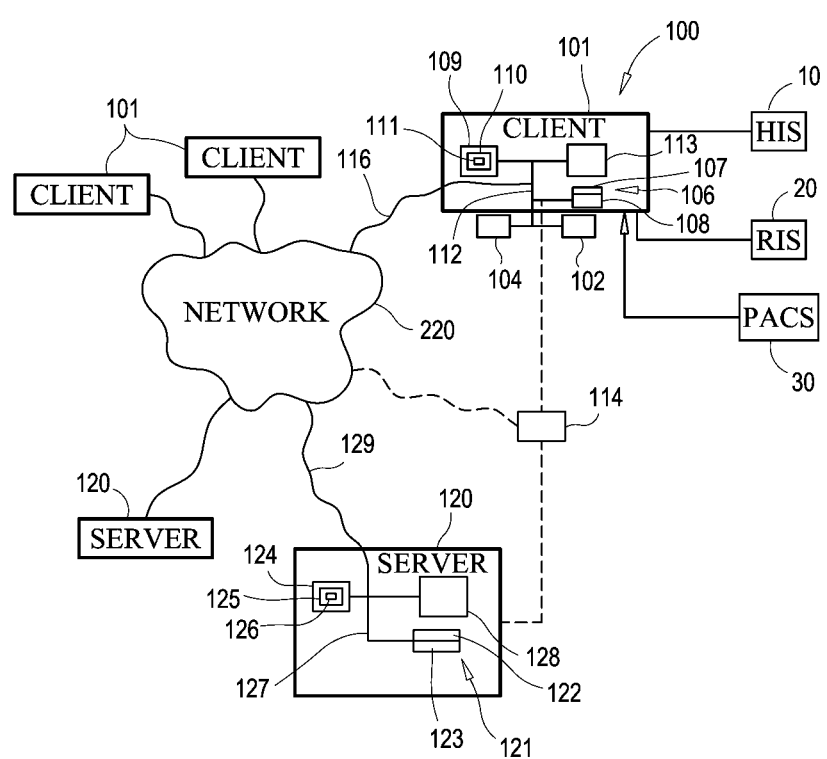
FIG. 1 is a schematic showing an electronic image workflow system in accordance with non-limiting example embodiments.

The aspects, advantages and/or other features of example embodiments of the present inventions will become apparent in view of the following detailed description, which discloses various non-limiting embodiments. In describing example embodiments, specific terminology is employed for the sake of clarity. However, the embodiments are not intended to be limited to this specific terminology. It is to be understood that each specific element includes all technical equivalents that operate in a similar manner to accomplish a similar purpose.

Existing productivity and economic measures do not take into account differences in workflow, technology, and clinical outcomes. Creation of a data-driven productivity workflow index would serve the purposes of more accurately measuring user and context-specific performance along with providing valuable feedback for determining best practice guidelines. Thus, provided herein are methods, apparatuses, systems, machine readable medium and computer readable program products that enable one to more accurately measure productivity of a workflow process.

It should be understood that example methods, apparatuses, systems, machine readable medium, and computer readable program products described herein may be adapted for many different purposes and are not intended to be limited to the specific example purposes set forth herein.

As used herein, "a" or "an" may mean one or more. As used herein, "another" may mean at least a second or more.

A number of supporting technologies may be used in accordance with example embodiments provided herein, including, but not limited to the following:
1. Electronic Auditing Tool (See U.S. patent application Ser. No. 11/586,580, which is hereby incorporated herein by reference in its entirety);
2. PACS (Picture Archival and Communications System);
3. EMR (Electronic Medical Record);
4. CPOE (Computerized Physician Order Entry);
5. RIS (Radiology Information System);
6. HIS (Hospital Information System); and
7. QA (Quality Assurance) Scorecards (See U.S. patent application Ser. No. 11/699,349, which is hereby incorporated herein by reference in its entirety)

Example embodiments are generally directed to methods of determining at least one Productivity Workflow Index (PWI) based on data regarding human computer actions and workflow-related variables.

By way of non-limiting example, methods may include electronically auditing and recording individual human computer actions an end-user goes through in the performance of a computer-based task (see e.g., U.S. patent application Ser. No. 11/586,580). The human computer actions in performing a computer-based task are the electronic workflow sequences that may be performed by a user, for example to selectively review information, such as images (e.g., a subset of clinically pertinent images from an entire imaging dataset. This human computer action data in turn may be automatically entered into one or more electronic databases using an extensible markup language (XML) schema, which allows for a number of downstream applications including (but not limited to) automated playback capabilities, detailed workflow analysis, and correlation with clinical data to perform outcomes analysis. The structured data derived from the electronic auditing tool may be standardized in a manner that is independent of the technology utilized, individual end-user, patient and institutional profiles. By standardizing this input data, meta-analysis can be performed over a wide population of end-users, thereby providing a mechanism to obtain large pooled data for detailed analysis.

Human computer actions may include actions performed for example, on a computer, workstation, portable device, etc., and an input device for the user's actions may include for example, a keyboard or a programmable stylus or other input device, that captures actions that are performed on an image displaying device.

According to non-limiting example embodiments, methods and systems of capturing user computer actions that may be used in accordance with the present inventions, are described for example in U.S. patent application Ser. No. 11/586,580, portions of which are described hereinbelow and in FIG. 1 (in addition to being incorporated herein by reference).

According to example embodiments, such as that depicted in FIG. 1, bi-directional communications between the electronic workflow system 100 and the information systems, such as the HIS 10, RIS 20, and PACS 30, etc., allows the electronic workflow system 100 to retrieve information from these systems, update information therein and provide the desired workflow templates that are generated by the electronic workflow system 100.

According to example embodiments, the electronic workflow system 100 may include a client computer 101, such as a PC (personal computer), which may or may not be interfaced or integrated with the PACS 30. According to example embodiments, an imaging display device 102 is included that is capable of providing high resolution of digital images in 2-D or 3-D, for example. According to other embodiments, the client computer 101 may include a mobile terminal, such as a mobile computing device, or a mobile data organizer (e.g., PDA), that is operated by the user accessing the program remotely from the client computer 101.

According to example embodiments, methods and systems may be carried out by providing an input mechanism 104 (see FIG. 1), or user selection device, including hot clickable icons etc., or selection buttons, in a menu, dialog box, or a roll-down window of an interface that is provided at the client computer 101. According to example embodiments, commands may be input through a programmable stylus, keyboard, mouse, speech processing system, laser pointer, touch screen, or other input mechanism 104.

According to example embodiments, the input or selection mechanism 104 may be a dedicated piece of hardware. Alternatively, the functions of the input or selection mechanism 104 may be executed by code instructions that may be executed on the client processor 106. According to example embodiments, the display unit 102 may display the selection window and a stylus or keyboard for entering a selection, for example.

As described in co-pending U.S. patent application Ser. No. 11/512,199, filed Aug. 30, 2006, which is hereby incorporated by reference in its entirety, a multi-functional programmable navigational stylus 104 may be provided to enable input of gestures, symbols, and/or icons through the imaging display device 102. According to example embodiments, other actions may be performed by the multi-functional programmable navigational stylus 104 that are intrinsic to the image display device 102, such as navigation, interpretation, and electronic workflow processes. The actions performed by the multi-functional programmable navigational stylus 104 on the image display device 102 may be superior to actions that are performed using traditional computer keyboard or mouse methods, both within the PACS and EMR.

The client computer 101 typically includes a processor 106 that operates as a client data processing device. The processor 106 may include a central processing unit (CPU) 107 or parallel processor and an input/output (I/O) interface 108, a memory 109 with a program 110 having a data structure 111, wherein all of the components are connected by a bus 112. Further, the client computer 101 may include an input device or means 104, a display 102, and may also include one or more secondary storage devices 113. The bus 112 may be internal to the client computer 101 and may include an adapter for receiving a keyboard or input device 104 or may include external connections.

According to example embodiments, the imaging display device 102 may comprise a high resolution touch screen computer monitor. According to example embodiments, the imaging display device 102 may be configured to allow images, such as x-rays, to be readable and for the gestures or symbols to be applied easily and accurately. Alternatively, the imaging display device 102 can be other touch sensitive devices including tablet, pocket PC, and plasma screens. The touch screen would be pressure sensitive and responsive to the input of the stylus 104, which may be used to draw the data gestures or symbols of the present invention, directly onto the image displaying device 102.

According to example embodiments, high resolution goggles may be used to provide end users with the ability to review images without the physical constraints of an external computer. For example, a surgeon may wear specialized high resolution goggles to display the cross-sectional radiological image of a brain tumor in 3-D format and may note markings on the image, to highlight the pathology in question and to report pertinent characteristics (i.e., anatomic localization, size, etc.), to serve as a guide during surgery. These goggles may be used for image-guided surgery and gesture-based reporting, for example, such as disclosed in co-pending U.S. patent application Ser. No. 11/176,427, filed Jul. 8, 2005, the contents of which are herein incorporated by reference, and may serve to view images in an electronic workflow system on pertinent findings during the course of surgery.

According to other embodiments, an internal medicine physician may use these specialized goggles to review images with embedded gestures or symbols, or text. The images could be downloaded using wireless technology and displayed on the goggles, thereby eliminating the need for a computer screen for image display.

According to example embodiments, the graphical user interface associated with the client computer 101 may be a client application that is written to run on existing computer operating systems. According to one embodiment, the client application may be ported to other personal computer (PC) software, personal digital assistants (PDAs), and cell phones, and any other digital device that has a screen or visual component and appropriate storage capability.

The processor 106 at the client computer 101 may be located internal or external thereto, and may execute a program 110 that is configured to include predetermined operations. The processor 106 may access the memory 109 in which may be stored at least one sequence of code instructions comprising the program 110 and the data structure 111 for performing predetermined operations. The memory 109 and program 110 may be located within the client computer 101 or may be located external thereto.

Note that at times systems and methods herein may be described as performing certain functions. However, one of ordinary skill in the art will readily appreciate that the program 110 may be performing the function rather than the entity of the system itself.

According to example embodiments, the program 110 that runs the electronic workflow method and system may include a separate program code for performing a desired operation or may be a plurality of modules that perform sub-operations of an operation, or may be part of a single module of a larger program 110 providing the operation. The modular construction facilitates adding, deleting, updating and/or amending modules therein and/or features within the modules.

According to example embodiments, the processor 106 may be adapted to access and/or execute a plurality of programs 110 that correspond to a plurality of operations. An operation rendered by the program 110 may include, for example, supporting the user interface, performing data mining functions, performing e-mail applications, etc.

According to example embodiments, the data structure 111 may include a plurality of entries, each entry including at least a first storage area that stores the databases or libraries of gesture symbols, or image files, for example.

According to example embodiments, the storage device 113 may store at least one data file, such as image files, text files, data files, audio, video files, etc., in providing a particular operation. According to example embodiments, the data storage device may include, for example, a database, such as a distributed database that is connected via a network, for example. According to example embodiments, the database may be a computer searchable database. According to example embodiments, the database may be a relational database. According to example embodiments, the storage device 113 may be connected to the server 120 and/or the client computer 101, either directly or through a communication network, such as a LAN or WAN. According to example embodiments, an internal storage device 113, or an external storage device 114 is optional, and data may also be received via a network and directly processed.

According to example methods and systems, a client computer 101 may be connected to other client computers 101 and/or servers 120, including administration, billing or other systems. According to example embodiments, the connections may be provided via a communication link 116 as a client communication means, using a communication end port specified by an address or a port. According to example embodiments, the communication link 116 may include a mobile communication link, a switched circuit communication link, or may involve a network of data processing devices such as a LAN, WAN, the Internet, or combinations thereof. In particular, the communication link may be to e-mail systems, fax, telephone, wireless communications systems such as pagers and cell phones, wireless PDA's and other communication systems.

According to example embodiments, the communication link 116 may be an adapter unit capable of executing various communication protocols in order to establish and maintain communication with the server 120, for example. According to example embodiments, the communication link 116 may be constituted by a specialized piece of hardware or may be realized by a general CPU that executes corresponding program instructions. According to example embodiments, the communication link 116 may be at least partially included in the processor 106 to execute corresponding program instructions.

According to example embodiments, if a server 120 is used in a non-distributed environment, the server 120 may include a processor 121 having a CPU 122 or parallel processor, which is a server data processing means, and an I/O interface 123. According to example embodiments, the server 120 may be constituted by a distributed CPU 122, including a plurality of individual processors 121 that are located on one or a plurality of machines. According to example embodiments, the processor 121 of the server 120 may be a general data processing unit. According to another embodiment, the processor 121 may include a data processing unit having large resources (i.e., high processing capabilities and a large memory for storing large amounts of data).

According to example embodiments, the server 120 may include a memory 124 with program 125 having a data structure 126, wherein all of the components may be connected by a bus 127. According to example embodiments, the bus 127 or similar connection line may include external connections, if the server 120 is constituted by a distributed system. According to example embodiments, the server processor 121 may have access to a storage device 128 for storing preferably large numbers of programs for providing various operations to the users.

According to example embodiments, the data structure 126 may include a plurality of entries, each entry including at least a first storage area which stores image files, for example. According to an alternative embodiment, the data structure 126 may include other stored information as one of ordinary skill in the art would appreciate.

According to example embodiments, the server 120 may be a single unit. According to an alternative embodiment, the server 120 may be a distributed system of a plurality of servers 120 or data processing units, and may be shared by multiple users in direct or indirect connection to each other. According to example embodiments, the server 120 may execute at least one server program for a desired operation, which may be needed in serving a request from the client computer 101. According to example embodiments, the communication link 129 from the server 120 may be adapted to communicate with a plurality of clients.

According to example embodiments, methods may be implemented in software that may be provided in a client and server environments. According to example embodiments, methods may be implemented in software that can be provided in a distributed system over a computerized network across a number of client systems. Thus, in the present invention, a particular operation may be performed either at the client or the server, at the edge of a network or at the center, or both. Therefore, at either the client or the server, or both, corresponding programs for a desired operation/service are available.

According to example embodiments, in a client-server environment, at least one client computer 101 and at least one server 120 are each connected to a network 220 such as a Local Area Network (LAN), Wide Area Network (WAN), and/or the Internet, over communication links 116, 129. Further, even though the systems HIS 10, RIS 20, and PACS 30 (if separate) are shown as directly connected to the client computer 101, it is known that these systems may be connected to the client over a LAN, WAN, and/or the Internet via communication links. According to example embodiments, interaction with users may be through secure and non-secure internet connectivity. Thus, the steps in the methods consistent with the present invention are carried out at the client computer 101 or at the server 120, or at both. According to example embodiments, the server 120 may be accessible by the client computer 101 over for example, the Internet using a browser application or the like.

According to example embodiments, the client computer 101 may communicate via a wireless service connection. According to example embodiments, the server system 120 may communicate with network/security features, via a wireless server, which connects to, for example, voice recognition. However, one of ordinary skill in the art will appreciate that other systems may be included.

In other embodiments, the client computer 101 may be a basic system and the server 120 may include all of the components necessary to support the software platform. Further, the present client-server system may be arranged such that the client computer 101 may operate independently of the server system 120, but that the server system can be optionally connected. In the former situation, additional modules may be connected to the client computer 101. In another embodiment consistent with the present invention, the client computer 101 and server system 120 may be disposed in one system, rather being separated into two systems.

Although the above physical architecture has been described above as client-side or server-side components, one of ordinary skill in the art will readily appreciate that the above components of the physical architecture may be in either client or server, or in a distributed environment.

Further, although the above-described features and processing operations may be realized by dedicated hardware, or may be realized as programs including code instructions executed on data processing units, it is further possible that parts of the above sequence of operations may be carried out in hardware, whereas other of the above processing operations may be carried out using software.

The underlying technology allows for replication to various other sites. Each new site may maintain "state" with its neighbors so that in the event of a catastrophic failure, other server systems can continue to keep the application running, and allow the system to load-balance the application geographically as required.

Further, although aspects are described herein as being stored in memory, one of ordinary skill in the art will appreciate that all or part of the methods and systems consistent with the present invention may be stored on, or read from, other computer-readable media, such as secondary storage devices, like hard disks, floppy disks, CD-ROM, a carrier wave received from a network such as the Internet, or other forms of ROM or RAM either currently known or later developed. Further, although specific components of the system have been described, one skilled in the art will appreciate that the system suitable for use with the methods and systems, may contain additional or different components.

Accordingly, in example embodiments, the electronic workflow system 100 and method as used in an exemplary radiology method and system, includes a client computer 101 with image displaying device 102, and an input device 104, such as a programmable stylus 104 as an input mechanism. According to example embodiments, the programmable stylus 104 may be used to perform other tasks that are intrinsic to the image display, navigation, interpretation, and reporting processes.

However, although examples described herein are in radiology, one of ordinary skill in the art would recognize that the present invention would be applicable for other medical disciplines, such as navigating through complex datasets, including, for example, endoscopy, cardiology, neurology, and surgery.

According to example embodiments consistent with the present invention, the radiologist may turn on the client computer 101, which may be a stand-alone PC, or connected to a client workstation known in the radiological field as the PACS workstation 30. In this exemplary embodiment, the client computer 101 may be the PACS 30, and some or all of the present invention, with respect to the imaging display device 102, computer memory 109 and program 110 etc., may be contained within the PACS 30 instead of being provided separately. According to example embodiments, the user may log onto the PACS system 30 once the client computer 101 is operational.

According to example embodiments, the program 110 and/or program 125 may include an electronic auditing function that enables capturing of "fundamental" data that is part of and contained within the radiologist electronic workflow system 100. According to example embodiments, the electronic auditing function may be configured to capture the individual steps that a radiologist performs during a complex process of medical image interpretation.

Figure 2:
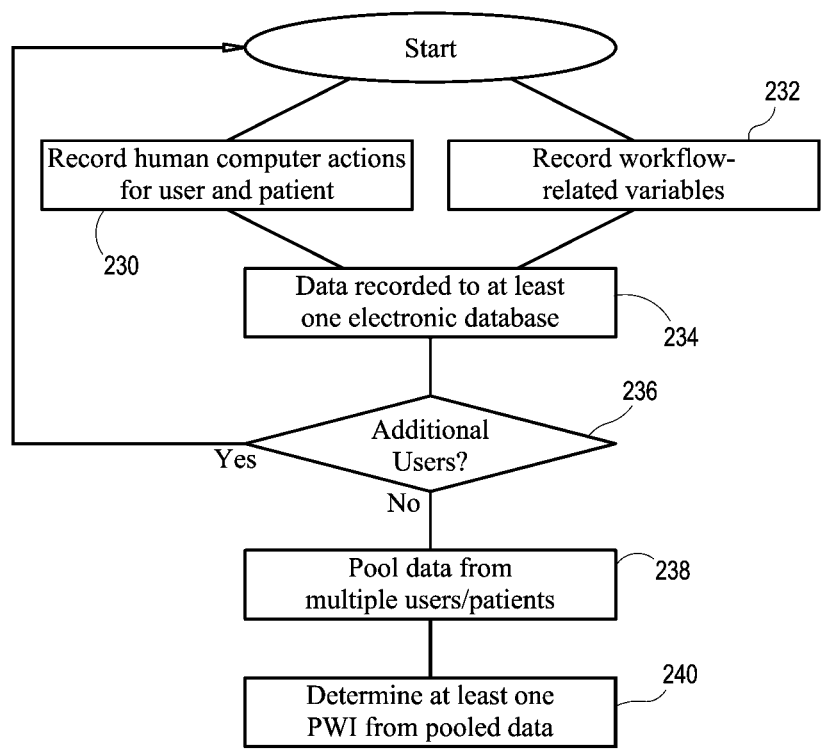
FIG. 2 is a flowchart of a method in accordance with non-limiting example embodiments.

Example methods may include for example, recording human computer actions by a first user relating to a first patient 230 (see FIG. 2); recording workflow related variables 232; recording data regarding the human computer actions and the workflow related variables to an electronic database 234; repeating the recording steps multiple times for the first user or a second or more users relating to a second or more patients 236; pooling the data 238; and determining at least one Productivity Workflow Index from the pooled data.

After detailed and stepwise-specific data has been recorded, multiple analyses can be performed to document the various steps different individual end-users go through to complete a specific process (e.g. radiologist interpretation of an imaging exam). The computer can in turn analyze any number of individual variables to ascertain variability in productivity and workflow among different end-users. Time-stamped and user-specific data may also be recorded into an electronic database for analysis. Thus, embodiments that include recording human computer actions, may include not only recording that a user performed certain activities (e.g., that certain information or databases were accessed by the user, or certain reports generated), but also may include time-stamping the human computer actions, so data is available regarding the time spent performing each activity.

Figure 3:
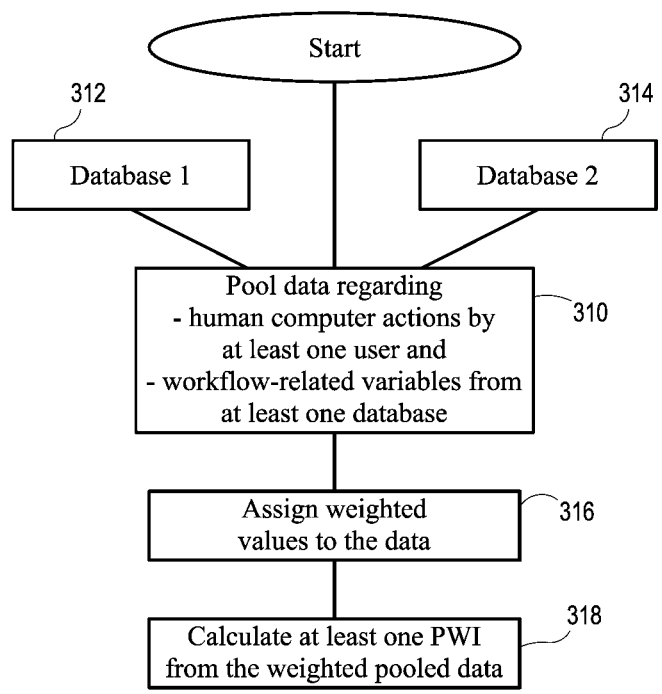
FIG. 3 is a flowchart of a method in accordance with non-limiting example embodiments.

Other example methods may include determining at least one Productivity Workflow Index using data regarding human computer actions and workflow-related variables, where the data may be obtained from other sources that have been recorded on at least one accessible database. By way of non-limiting example, such methods may include pooling data regarding human computer actions by a user and workflow-related variables 310 (see e.g., FIG. 3) from at least one electronic database (e.g., 312, 314); and determining at least one Productivity Workflow Index from the pooled data 318. PWI scores may be determined for example, by assigning weighted values to particular data 316. A list of potential PWI data sources according to non-limiting example embodiments includes the following: PACS, RIS, EMR, Imaging Modality, CPOE, Electronic Auditing Tool, and QA Scorecards.

According to example embodiments, the human computer actions may include various activities by a user, for example, a user's workflow at a computer or terminal, such as with respect to reviewing a patient's history, reviewing and/or generating reports, reviewing radiology images, and the like.

Workflow related variables according to example embodiments may include (but are not limited to) at least one variable selected from the group consisting of patient profile, institutional profile, technology used, clinical variables, exam variables, imaging variables, and outcomes analysis. Variables within a Medical Imaging workflow may include for example, imaging modality, anatomic region being imaged, number of image acquisitions, size of dataset, contrast administration, image processing/reconstructions, referring clinician, patient profile, patient physical characteristics (e.g. size), correlating imaging data, correlating clinical data (lab, pathology, testing), medical history, clinical indication, image quality, and decision support. Below is a more detailed list of example workflow related variables, including examples of types of factors that may be taken into account with respect to each variable. These variables are also discussed further below.

1. Patient profile (measure of patient compliance)
   a. Age
   b. Gender
   c. Genetics
   d. Body habitus
   e. Mobility
   f. Overall clinical status
2. Institutional profile (measure of operational efficiency)
   a. Location
   b. Patient population served
   c. Academic status
   d. Size
   e. JCHAO (Joint Commission on Accreditation of Healthcare Organizations) scores
   f. Operational efficiency measures
3. Clinical profile (measure of disease-specific complexity)
   a. Clinical indication
   b. Patient medical/surgical history
   c. Availability of clinical data (current and historical)
   d. List of active disease processes
   e. Ongoing treatment regimens
   f. Lab/clinical tests
4. Imaging profile (measure of complexity and volume of historical imaging data)
   a. Quality of imaging data
   b. Historical imaging exams
      indication specific
      modality specific
   c. Prior imaging reports
5. Technology profile (measure of supporting technology efficiency)
   a. Acquisition device (modality, e.g. CT scanner)
   b. Information system technology (RIS, PACS, EMR, CPOE)
   c. Processing technology (multiplanar reconstruction (MPR))
   d. Decision support tools (computer-aided detection (CAD))
   e. Reporting/communication
6. Exam profile (measure of size/complexity of dataset and tools used for analysis)
   a. Clinical indication
   b. Size/complexity of imaging dataset
   c. Image processing
   d. Data reconstructions
   e. Number of sequences
   f. Contrast administration
   g. Overall quality of data
7. Outcomes profile (measure of quality indicators and clinical outcomes (such as length of stay in hospital, time to initiate treatment, additional exams/tests, adverse actions, and morbidity/mortality))
   a. End-user comprehensive profile
   b. End-user task-specific profile
   c. End-user exam-specific profile
   d. End-user education and training
   e. Clinical feedback With regard to patient profile, a number of patient-specific factors may ultimately affect the technical and clinical success of an exam being performed. Physical and clinical patient-specific attributes may play a major part in the time and effort expended and would include patient body habitus, compliance, age, and underlying clinical condition. For example, an ambulatory 60 year-old male in excellent health who follows commands and freely communicates with staff will be far easier (and less resource intensive) then a 60 year-old male who is morbidly obese, non-communicative, and immobile. Even though the same exam type may be performed for each patient at the same institution, by the same staff, using the same technology; the effort required is far different.

Inter-institutional differences can ultimately affect differences in resource requirements. For example, the same exam type (chest CT) may be performed for the same clinical indication (i.e., lung cancer diagnosis) at two different institutions; the first being a tertiary care government ((Veterans Affairs (VA)) hospital and the second institution consisting of a for-profit community hospital. Both institutions utilize similar technologies to acquire the exam (i.e., CT scanner), interpret the exam (i.e., PACS), retrieve clinical data (i.e., EMR) and report the data (i.e., RIS). However, the VA hospital may have intrinsic deficiencies in workflow and productivity when compared with the community-based hospital, which ultimately impact time requirements for technologists who are performing the study, radiologists who are interpreting the study, and clinicians who are acting upon the study results. As a result, these institutional-specific differences may have an impact on the resource requirements to complete the same process and should be factored into the final workflow analysis.

Clinical differences may play a major role in differentiating workflow requirements given comparable patient, institutional, and technology variables. If we take the example of chest CT for lung cancer screening, we can look at two different clinical scenarios. In the first, the patient is a healthy 60-year old with no pre-existing medical history. In the second, the patient is also 60 years old, but has a pre-existing history of renal cell carcinoma, which has led to multiple prior hospitalizations, chemotherapy treatment regimens, and previous surgery. In the course of treatment and diagnosis of the renal cell carcinoma, this patient had multiple prior chest CT exams looking for metastatic disease. As a result, the interpretation of the current lung cancer screening CT will require correlation with the prior chest CT exams along with meticulous review of the patient's medical record (contained within the EMR). Both of these time intensive tasks would not be required for the comparison patient in excellent health and no pre-existing medical history.

While not frequently considered in workflow analysis, the quality (and quantity) of the imaging data (i.e., imaging variables), is an important component in determining resource requirements (in addition to clinical outcomes). Let us suppose that the same patient undergoes the same exam (chest CT for lung cancer screening), using the same technology, and the same clinical history. In the first case, the patient is highly cooperative and the technologist performing the study extremely vigilant. The resulting imaging dataset transferred to the radiologist is of exceptionally high quality and requires minimal effort (on the part of the radiologist) for image processing and manipulation, to render a diagnosis. The alternative scenario is that of the patient and/or technologist who is not compliant or vigilant, resulting in a limited quality CT exam with significant motion artifact. This motion artifact hampers the radiologist in his/her ability to render a definitive and accurate interpretation. As a result the radiologist may be tasked with greater time requirements to review/manipulate the data or introduce terms of uncertainty into the report to qualify the interpretation accuracy. The net effect is that one exam was expeditiously interpreted with high degree of diagnostic confidence while the other exam was equivocated and delayed in diagnosis.

Differences in technology may play a critical role in productivity and workflow variability. In the example of a chest CT (e.g., for lung cancer screening), a number of different technologies are utilized in the imaging cycle including the CT scanner used to acquire the imaging data (i.e., acquisition device), PACS used to transmit, store, and display the exam, decision support technologies used to facilitate image processing (e.g. MPR) and interpretation (e.g. CAD), to the reporting system used to communicate clinical data (i.e. RIS).

One can easily see that any differences in the technology used for any or all of these processes can have a profound impact on productivity and workflow (in addition to clinical outcomes). For example, a ten year-old CT scanner purchased on the after market with somewhat antiquated software will not be as productive (nor produce the same image quality) as the state-of-the-art CT scanner. The output (e.g. size and complexity of the imaging data) from these two comparable acquisition devices may be vastly different as well, thereby creating different end-user expectations in clinical outcomes.

The exam profile may include multiple variables attributed to the specific imaging dataset acquired and processed. In addition to exam type (e.g., brain MRI), a number of technical parameters are recorded which contribute to the overall size and complexity of the dataset. These may include acquisition parameters, number of sequences obtained, image processing applied to the raw data, reconstruction algorithms, and contrast administration. The clinical data specific to that exam (i.e., clinical indication) would also be incorporated into the exam profile, which provides valuable information in determining the exam protocol utilized. Another important variable contained within the Exam profile is quality assessment score, which provides a quantitative measure (which can both subjective and objective in nature) of image quality. A detailed explanation of how quantitative and reproducible quality scores can be derived is contained within e.g., U.S. patent application Ser. No. 11/699,349.

An important variable contributing to productivity/workflow assessment is outcomes analysis. This entails longitudinal analysis of multiple comparable data elements to identify a cause and effect relationship that is associated with improved (or reduced) measures of clinical outcomes. These outcome analyses can take a number of different forms and could include (but are not limited to) time to initiate clinical management, accuracy of diagnosis, morbidity/mortality, and length of hospitalization stay. While these do not measure productivity/workflow (which occurs at the time of process completion), it does represent an extremely valuable measure of operational "success," and as a result should be factored into the final analysis of measuring workflow/productivity.

Data regarding human computer actions and workflow-related variables may be recorded at the same or different times, from the same and/or different sources. For example, some data regarding workflow-related variables may already be included in a database or automatically populated into a database (such that it may optionally be modified by the user) before any human computer actions take place, such as information regarding equipment, location, institutional profile and the like. Many workflow-related variables may be recorded at the time of human computer actions. Further workflow-related variables may be recorded after human computer actions are recorded, or may not be available for some time (such as outcome variables). Thus, an outcome input may be initially left blank, or populated (at least temporarily until actual outcome data is available) using average user outcome, e.g., for similar cases, or average outcome for that user overall.

A pooled PWI score may be determined with respect to various pooled groups of data or PWI scores depending on the information sought. By way of non-limiting example, a pooled PWI score may be determined for an individual, which includes all of that individual's PWI scores (e.g., for different patients). Another pooled PWI score may be determined for a particular facility (e.g., Hospital X) or type of facility (e.g., radiology centers). A different pooled PWI score may be determined for a particular location or type of location (e.g., World, U.S., North America, Mid-Atlantic U.S., urban, or rural). Alternatively a PWI score may be determined based on the profession/expertise of the user with respect to the actions being performed (e.g., radiologist, primary care physician, technician, etc.). Further, example pooled PWI scores may be determined based on the resources available to the users, for example, pooled PWI scores may be determined for only users having particular equipment. Other pooled PWI scores may be determined based on the workflow being performed, e.g., for all CT exams. Further, example pooled PWI scores may be provided based on combinations of these types of groups. For example, a pooled PWI score may be determined for radiologists in urban, mid-Atlantic hospitals, or for primary care physicians in rural areas, etc. Thus, according to non-limiting examples a Productivity Workflow Index determined by the present methods may be a PWI based on pooled data from at least one group of data selected from the group consisting of: common profession of users, common facility of users; common geographic location of users, and common resources of users.

According to non-limiting embodiments, data regarding various groups may be maintained in a single database or a group of databases that may be accessed, such that a requestor of PWI information may set desired parameters for a PWI score to be determined (e.g., for a particular imaging center, or a particular doctor), and a PWI score may be calculated.

Pooled PWI scores may be for example a single score, or may include a range of scores. For example, if one were to query as to a pooled PWI score for radiologists, a single mean, median or other PWI score may be provided, and/or a range may be provided, e.g., depending on the distribution of data or PWI scores in the pool. For example, in a bell curve distribution of individual PWI scores in the pool, a range encompassing the $25^{th}$ to $75^{th}$ percentile scores may be provided alone or in combination with the mean or median PWI score. Alternatively, the full range of PWI scores may be provided. In yet other embodiments, the raw data may be combined as if it was a single individual, and analyzed to determine a single PWI score.

According to example embodiments, Productivity Workflow Index (PWI) may be determined from a pooled set of data or from data regarding a single user. PWI scores may be determined using for example, a weighting system, where certain individual data elements, such as certain actions and variables, may be assigned a particular numerical value. The time spent on each activity may also play a role in determining a PWI score.

According to non-limiting example embodiments, weighted numerical values can be assigned (based e.g., on comprehensive data analysis) based on these individual data elements which in turn can be summed to determine the productivity-workflow index (PWI), which collectively takes into account clinical challenges (e.g. patient compliance, past medical/surgical history, clinical indication), resource expenditures (e.g. time, technology, personnel), data quality (of current and past imaging/clinical data), overall clinical outcomes (morbidity/mortality, diagnostic accuracy, timeliness to care), and other factors.

Example methods may include determining a PWI for a single user based on recorded data regarding that user's human computer actions and workflow-related variables. As with other example methods the PWI for a single user may be calculated for example by assigning weighted values to the recorded data. Such example methods may include actually recording data (optionally including data regarding time spent performing actions), or it may include accessing data recorded on one or more databases.

Methods provided herein may further include determining a PWI score for a single user based on that user's human computer actions and workflow-related variables; and comparing the PWI for the single user, to at least one PWI from the pooled data. The comparison may be provided for example by use of a ratio, or in the case where the PWI for a pool of individuals is provided by a range, the comparison may be a determination of how the single user's PWI compares to the range, median and/or mean of the pooled data.

According to example embodiments, using such comparisons to pooled information, an individual or his or her supervisors may be able to gauge how productive he or she was on a particular task, on a particular type of task, or over a period of time, as compared to one or more peer groups of other like professionals, others in the same facility, others with like facilities or resources, others in the same region, etc. Thus, according to non-limiting example embodiments, the pooled data may be selected from the group consisting of pooled data from users at the same facility as the single user, pooled data from a common profession of users as the single user, pooled data from a common geographic location of users as the single user, and pooled data from users having common resources as the single user.

According to example embodiments, a user's PWI score, or data regarding recorded human computer actions by a single user and data regarding the recorded workflow related variables relating to the single user, may be determined for a single user based on data regarding a single patient, or it may include data for that individual with respect to multiple patients, e.g., for a particular type of patient or activity or over a certain period of time.

According to example embodiments, an individual user's PWI may be initially determined at the time of performing a particular task. In such instances data regarding the outcome may not yet be available for that particular patient. Thus, for purposes of determining the immediate PWI score (or estimated score), outcome data may be substituted (at least temporarily), based on for example, average outcome data for that user, or for users in that facility or for users in a like peer group for that type of analysis. Then, if desired, an actual PWI may be later determined after actual outcome data is later obtained. For purposes of updating pooled databases for determination of pooled PWI scores, the individual's data may not be used until the actual outcome data and/or actual PWI score is determined.

Methods provided herein may further include determining a PWI score for a first pooled group of users based on human computer actions and workflow-related variables within the pooled group; and comparing the PWI for the first pooled group, to at least a second pooled group of users and patients. The comparison may be provided for example by use of a ratio, or in the case where the PWI for a pool of individuals is provided by a range, the comparison may be a determination of how the single user's PWI compares to the range, median and/or mean of the pooled data.

According to example embodiments, using such comparisons of one pooled group to another, an administrator, insurance company or other group or facility may be able to determine how one facility compares to others (e.g., in the region), how radiologists compare to all users in the hospital, etc. . . .

Comparisons of pooled PWI scores may be used not only with respect to evaluation by a facility of a particular user or to determine compensation, but also for a user to determine real time if there is additional information they can seek or additional tasks to be performed that might increase their productivity. According to such examples, PWI scores (at least estimated scores) and/or comparisons to pooled PWI scores may be calculated at various stages during an actual process, which may prompt a user to perform additional steps or query as to what additional steps/actions may be recommended to increase the PWI score (which should translate overall to better patient outcomes).

Also provided are computer-implemented methods for providing an estimated completion time for a workflow process in the medical field, which include determining at least one estimated Productivity Workflow Index for a workflow process by assigning weighted values to recorded data regarding human computer actions and workflow-related variables, where the Productivity Workflow Index includes information regarding an estimated completion time for a workflow process or portions thereof; and displaying estimated completion time information to the user performing the workflow process. Such methods may include various ways in which a user may "pace" their workflow, for example as decided by the user. The "pacer" may be an automated function that alert a user for example if productivity and workflow measures exceed expected measures (i.e., too slow or too fast), for example at various time periods (e.g., one quarter or one half of the way through the workflow process). The estimated completion time may be for example, time until overall completion of the workflow process, thus the pacer may include a clock function to tell a user how much time has passed (or how much time remains) in the workflow as compared to a reference PWI in a similar process, or the pacer may include periodic updates of time expended or remaining the workflow process as compared e.g., to time expended or remaining at a common interval with a reference PWI in a similar process. Thus, the estimated completion time may be for example, time until overall completion of the workflow process, completion of a portion of the workflow, running clock information, and countdown clock information.

Example embodiments are also directed to apparatuses that include a server and software capable of performing methods herein or portions thereof. By way of non-limiting example, software may be capable of determining various pooled and individual PWI scores. For example, the software may be capable of pooling data regarding human computer actions by a user and workflow-related variables from at least one electronic database and determining at least one Productivity Workflow Index from the pooled data, for example by assigning weighted values to the data. The software may also be capable of determining a Productivity Workflow Index for a single user e.g., by assigning weighted values to data regarding that user's human-computer actions and workflow-related variables. The software may further be capable of comparing the Productivity Workflow Index for the single user to at least one PWI from the pooled data.

The software may optionally be capable of determining at least one Productivity Workflow Index (pooled and/or individual) using information contained in at least one database, which is not necessarily recorded using the same software. Information regarding human computer actions and/or workflow-related variables may be accessed by the server by various methods. The information may be stored in one or more databases that may be accessed separately, such as over the internet or in a database coupled to the server (as in the systems described below).

Example embodiments also include systems that include a server coupled to a database. The database may be one or more databases that include information regarding recorded human computer actions by at least one user and at least one patient and information regarding workflow-related variables. As with other embodiments, in example embodiments, the server may include software capable of performing the methods herein, or a portion of such methods. For example, such software may be capable of determining at least one Productivity Workflow Index from data contained in the database(s). The server may include software capable of recording human computer actions by a first user, relating to a first patient; recording workflow related variables; recording data regarding the human computer actions and the workflow related variables to an electronic database; repeating the recording steps multiple times for a second or more users, relating to a second or more patients; pooling the data; and determining at least one Productivity Workflow Index from the pooled data. According to example embodiments, the software may further be capable of comparing data regarding recorded human computer actions by a single user, and data regarding the recorded workflow related variables relating to the single user (for example, by determining an individual's actual or estimated PWI score), to a Productivity Workflow Index for a pool of individuals.

Example embodiments are also generally directed to a machine readable medium (such as a computer readable medium) that include code segments embodied on a medium that, when read by a machine, cause the machine to perform any of the present methods or portions thereof. Thus, example embodiments of a machine readable medium may include executable instructions to cause a device to perform one or more of the present methods or portions thereof.

Example embodiments also include computer-readable program products that include a computer-readable medium and a program for performing one or more of the present methods or portions thereof.

A medium (such as a machine-readable medium or computer-readable medium) may include any medium capable of storing data that can be accessed by a sensing device such as a computer or other processing device, such as for example, a PACS workstation or one or more dedicated processors. A machine-readable medium includes servers, networks or other medium that may be used for example in transferring code or programs from computer to computer or over the internet, as well as physical machine-readable medium that may be used for example, in storing and/or transferring code or programs. Physical machine-readable medium includes for example, disks (e.g., magnetic or optical), cards, tapes, drums, punched cards, barcodes, and magnetic ink characters and other physical medium that may be used for example in storing and/or transferring code or programs.

There are many possible applications for the present, methods, systems, etc. provided herein (in addition to those discussed above) including, but not limited to those listed below:
1. Tool for measuring exam complexity
2. Workflow distribution (based on end-user and exam profiles)
3. Productivity tool (pacer)
4. Administrative tool to assess productivity, technology utilization, and quality
5. QA tool
   a. Prospective identification of "problem cases"
   b. Incorporation of "double reads", sub-specialty consultations
   c. Determination of transition point where PWI and QA intersect
6. Business applications
   a. Service costs directly tied to exam difficulty (PWI) and QA deliverables
   b. Tool for adjusting medical malpractice rates
   c. Economic incentives for practitioners tied to PWI and QA Scorecards d. Registry for customers to select practitioners based on PWI/QA data
7. Educational feedback to identify end-users deficiencies
8. Identification of "best practice" guidelines based on PWI and QA scores
   a. Feedback to individual end-users
   b. Recommendations for integrating EMR/PACS data into workflow along with workstation tools and computer applications
   c. Automated workflow templates based on optimized PWI (See e.g., U.S. patent application Ser. No. See U.S. patent application Ser. No. 11/586,580)

The first application listed above, is a means to prospectively quantify the complexity and associated time requirements for a proposed task, which could include any number of medical-related processes such as interpretation of an imaging study (e.g. radiologist), acquisition of a dataset (e.g. technologist), performance of a consultation (e.g. cardiologist), or performance of an operative procedure (e.g. surgeon). The individual who is assigned the task at hand could enter into the computer the pertinent input data (i.e. patient name, procedure to be performed, and location of service). The computer may in turn search the PWI databases to identify the individual and collective PWI scores from each respective database (patient, institution, service provider, technology) and calculate a number of PWI scores along with corresponding time estimates associated with them. If for example, a surgeon is planning a thoroscopic chest procedure on a patient, the PWI score would be calculated based on that specific surgeon's operative history for that specific procedure, along with modifiers based on the institution the procedure will be performed at, the corresponding technology to be used, and the patient and clinical profile data.

In addition to this operator-specific PWI data, the PWI databases can be searched to provide correlating peer data from other surgeons on a local, regional, national, or international level to serve as a reference. The operator (e.g. surgeon) could elect to review this peer data in greater detail to identify causative factors that may cause peer PWI data to be higher or lower than his/her own. As an example, a surgeon (Dr. Jones) identifies that a colleague has a 15% lower time estimate for completing the same operative procedure (given the same clinical, patient, institutional, and technology profiles). Dr. Jones may query the computer to provide a comparative workflow analysis. In this analysis, the computer may present Dr. Jones with a side-by-side workflow analysis, which highlights workflow differences between himself and the more efficient surgical colleague. Dr. Jones could in turn elect to utilize this information to modify his workflow for the proposed procedure and/or create a new automated workflow template. In addition to providing a measure of exam complexity and time requirements, the computer could also search the outcomes database to provide retrospective analysis of expected clinical outcomes (for that given task) and the frequency distribution and specific types of adverse outcomes.

In the example of a surgeon preparing for a specific procedure, the PWI search of the outcomes database may identify the most frequent surgical complications associated with the planned procedure (given the patient, technology, and institutional profile data). The surgeon can in turn utilize this data to prepare him/herself for those specific steps most prone to error and prospectively utilize targeted on-line educational programs for a quick review and remedial education. In the proposed example, the surgeon may learn that a specific surgical technique has a higher morbidity and mortality than an alternative surgical option (for that specific patient profile), and elect to utilize this alternative technique. In addition to providing PWI and workflow data specific to this alternative surgical technique, the computer can search on-line educational programs to identify a series of tutorials specific to that procedure and provide the surgeon with links that can automatically be reviewed. In the event the surgeon elects to review one of the educational programs, this data will be recorded in the surgeon's database.

The second potential application listed above of PWI applications is the ability to automate workflow distribution, in accordance with PWI database information. In this example, an integrated hospital network (e.g. within the Veterans Affairs) may be using the PWI database to distribute large volumes of imaging exams for radiologist interpretation through teleradiology. Once the technologist completes each exam, it is automatically downloaded into a comprehensive imaging database for distribution. A pool of radiologists may be available at any given point of time and the computer intelligently assigns the exams to be read to each individual radiologist based on PWI data analysis. For purposes of the example three different exams are looked at; a chest radiograph performed on an ICU patient, a vascular ultrasound evaluating deep venous thrombosis (i.e. blood clot), and a post-operative/radiation neck CT following treatment of head and neck cancer. In each case, the PWI exam-specific databases are searched and cross-referenced with the radiologist-specific PWI databases, with the goal of achieving the optimal and most efficient match (based on the available pool of radiologists). For the chest radiograph, the various PWI databases are queried and a range of PWI scores are derived which correspond to each individual radiologist who is currently "active" within the network and have clinical privileges for the specific exam (portable chest radiograph) to be interpreted. The PWI analysis reveals a sub-group of radiologists with the lowest PWI workflow scores and highest outcomes analysis (given that specific exam's patient, institutional, clinical, and technology profiles). The determination of "acceptable PWI thresholds" can be established automatically (based on statistical analysis of national PWI databases) or manually (by the local hospital/radiology administrator). For this example, 12 radiologists (out of the total of 110 "active" radiologists) are identified as "high PWI" candidates. Based on each of the 12 radiologists working queues (of unread exams), an automated distribution is performed, assigning the exam to be read to that "qualifying" radiologist with the shortest queue. This automated workflow distribution model serves to maximize exam throughput, while achieving the optimal clinical outcomes analysis based on quantitative analysis of technical, clinical, and educational factors.

The same type of analysis if automatically performed for the other two example exams (vascular ultrasound and neck CT), except in these cases the analysis is more complex based on the exam profiles. In the example of the venous ultrasound, the computer identifies 7 radiologists that meet the "acceptable PWI threshold". However, several limiting factors are identified for this specific exam including the technologist performing the exam and the technology being used. The performing technologist has been identified (based on combined analysis of the PWI and QA Scorecard databases) as having lower performance metrics than their peer group. At the same time, the technology profile identifies the ultrasound equipment being used as also having PWI and QA metrics below the expected mean (due to the fact that this ultrasound until is 8 years old and does not have several features intrinsic to a newer unit). Based on analysis of these technologist and technology profiles, it is determined that the exam be placed into a special PWI profile group, which necessitates interpretation by a subspecialty-trained radiologist with a higher outcomes analysis profile. In this setting, only two "active" radiologists fulfill the criteria and the assignment is made based on which of the two radiologists has the shortest "waiting time" (which is derived by the unread exams on their queue and the estimated interpretation times for each study based on the PWI data). This "waiting time" is another unique feature of the PWI automated workflow in that prospective time measurements can be derived from each working queue, based on the number and type of exams on the queue, along with each individual exam's PWI score and corresponding estimated time to completion.

The third example of a potential application with respect to workflow distribution (post-operative/radiation neck CT) becomes even more complex in its analysis than the preceding two examples. Based on the patient's clinical and imaging profiles, an extremely high PWI score is derived due to the complexity of the patient medical/surgical history (including two prior neck surgeries, radiation therapy, and documented tumor recurrence) and past imaging history (which includes 4 comparison CT exams and 2 MRI exams). In this case, cross-referencing the exam and clinical specific PWI databases with those of the radiologist reader pool, no "active" matches are identified. Only 3 radiologists (out of a total pool of 185 radiologists) are identified as "qualified" readers for this exam, none of which are 'active" at that point in time. Based on the ordering data (derived form the RIS and CPOE), the examination is determined not to be "stat" and instead qualifies as a "routine" exam in terms of clinical urgency and interpretation timeliness. Based on this categorization of "routine", the pre-determined turnaround time (based on administrative input specific to each host institution) is 48 hours. When the computer reviews the radiologist on-line working schedules, it is determined that of the 3 "qualified" radiologists, the first available radiologist (Dr. Strong) will become "active" in 12 hours and will be prospectively assigned the case. In the event was pre-determined to be "stat", an emergent workflow schema would have been initiated, with the highest PWI "active" radiologist assigned the case, along with a requisite "second read" automatically required by one of the three "qualified" radiologists at a later date. This identifies another unique feature of the PWI invention; automated QA workflow tracking based on exam priority and multiple (clinical, radiologist, patient, technology) PWI measures.

The next potential application of the present methods is that of a productivity tool, which can in effect be used as a "pacer". When Roger Bannister achieved acclaim as the first human to break the 4 minute mile, he did so by utilizing 4 "rabbits" to serve as pacers. Each "rabbit" was assigned the task of running ¼ mile in 1 minute, thereby providing Roger Bannister with an effective and reliable means to maintain a steady and productive pace, and ultimately achieve the end-goal of running a 4 minute mile.

The PWI methods herein may provide a similar productivity "pacing tool" by utilizing PWI (and derived time) measures to provide an automated pacer, which the end-user can activate (i.e. turn on and off) at their own choosing. In the example of a radiologist interpreting a complex neurological brain MR study (consisting of a contrast enhanced brain MRI and brain MR arteriography), the radiologist can elect to utilize the pacing tool function. Below is an itemized example of how the tool may work according to non-limiting example embodiments:

1. Radiologist activates the pacer function on his/her computer toolbar.
2. When the exam is selected from the worklist, the PWI database is automatically queried to determine the comprehensive PWI score (based on the individual profile analyses) and estimated completion time.
3. This "estimated completion time" is presented to the radiologist immediately preceding image display.
4. The radiologist is then given a number of options by the computer in terms of "pacer options".
5. These pacer options may include (but not limited to) the following:
   a. Frequency with which pacer data is provided.
   b. Mode of pacer feedback.
   c. Option of automated versus manual workflow.
6. The radiologist can elect to select these pacer options manually for each individual exam or defer to an automated list of pre-selected pacer options (which are included in each individual radiologist profile and specific to each individual exam type).
7. In this example case, the radiologist manually selects the following pacer options:
   a. Frequency of pacer data notification: Quarterly intervals.
   b. Mode of pacer feedback: Voice
   c. Option of automated versus manual workflow: Manual.
8. The computer determines the estimated "exam completion time" is 8 minutes 20 seconds, based on the comprehensive PWI analysis.
9. As a result, the quarterly pacer notification will occur every 2 minutes 5 seconds in the form of a spoken voice, which notifies the radiologist that 25%, 50%, 75% or 100% of the estimated exam completion time has expired.
10. At any time in the interpretation process, the radiologist can turn the pacer off or switch from manual to automated workflow.
11. After completion of the task, the computer offers the option (selectively turned on or off) to the end-user of receiving individual and comprehensive workflow analyses based on the derived and actual pacer measurements.
12. Some of these data measures may include (but not limited to) the following:
   a. Individual exam (e.g. the most recent exam performed).
   b. Periodic exam statistics (e.g. all exams at hourly intervals).
   c. Exam-specific statistics (e.g. all head CT exams.)
   d. Patient-specific statistics (e.g. all exams on patient John Smith).
   e. Cumulative statistics (e.g. all exams performed during the course of that specific workday).
13. The data could be presented in a number of different formats, according to individual end-user preferences (e.g. bar graphs, numerical data, line plots).
14. The computer could provide the option to cross-reference this pacer data with a number of comparable data including outcomes analysis, cumulative fatigue measures, and automated workflow templates.

An analogous tool to the PWI-derived pacer function would be the PWI-workflow function. In this tool, the individual end-user's workflow and utilization of computer-based data would be compared to that of comparable users. If a specific function or tool was not utilized in the performance of a given task (e.g. coronal reconstructions for a chest CT angiogram in the assessment of pulmonary embolism), the computer can provide an alert to the end-user and the specific function that was not utilized. If for example, the radiologist attempted to sign off on a chest CT without reviewing the entire dataset or not utilizing a specific computer application commonly utilized, the workflow feedback tool could provide an alert to the end-user along with an automated option to apply the recommended function. This in effect serves as an intelligent reminder of potential tools or function which is overlooked in the course of a given task. Just as the case of the pacer tool, the end-user can elect to turn this application on or off at any given time. By having the capability of cross-referencing these data with those of the outcomes and PWI databases, it provides an automated means of creating "best practice" automated workflow templates.

Workflow templates may include for example XML schema having specific directions for performing clinical and imaging data extraction, such as image display, navigation, image processing, application of supporting decision support tools, report creation and communication protocols, among other functions.

The present methods, systems, apparatuses, machine-readable medium and computer-readable program products also provide unique and objective tools to facilitate various administrative analyses including staff productivity, technology utilization, operational efficiency, and service deliverables. As an example of how these administrative analyses can be performed in an automated fashion using databases, including PWI information, which may be readily calculated from such databases, or pre-calculated and maintained in such databases, a hospital-based radiology department may be analyzed (although the same type of administrative analyses could be performed within any other clinical department).

A number of tasks are routinely performed by radiology or hospital administrators, who are charged with maintaining high levels of operational efficiency, while also maintaining fiscal responsibility. The resources that currently account for the vast majority of operational costs include personnel and technology. The challenge for the administrator is to ensure that a wide array of service deliverables is maintained at a high level (which can include variables such as exam backlog, patient waiting times, patient throughput, report turnaround time, diagnostic accuracy, and communication of critical results). While a few of these variables can be electronically tracked through time stamped events on the HIS/RIS (e.g. report turnaround time), the majority of these are left to manual analysis, resulting in inefficient (often non-existent) and error-prone analyses. The structured data elements contained within the PWI databases provides an objective and automated mechanism for performing customized administrative analyses. By prospectively tracking these analyses, an administrator can not only perform trending analyses over time, but also correlate these operational efficiency measures with local, regional, or national reference groups. Relevant examples of how the PWI databases can be used are listed below:
 1. Administrator wants to determine technologist productivity within the radiology department and identify variation according to the individual technologist, type of exam, and technology used.
 2. Administrator wants to determine diagnostic accuracy of individual and collective radiologist interpretations and ensure that emergent results are communicated directly to the referring physician in a timely fashion.
 3. Administrator wants to determine the impact and variability of departmental staffing on exam backlog, patient waiting times, and exam throughput.

For assessment of technologist (or other staff) productivity, an administrator can search the PWI database profiles to compare the predicted versus actual PWI scores and examination times for each individual technologist. By doing so, the administrator can accurately and objectively identify the expected versus actual intra and inter-technologist productivity measures. Note that expected time estimates are calculated based on the various PWI input data. If the actual time exceeds the estimated time, one can assume the productivity is less than expected barring extenuating circumstances (e.g. equipment breakdown). If the actual time recorded is less than predicted (based on PWI input data), then productivity exceeds that which is expected. The relative impact different variables (e.g. technology, exam type, patient population) have on technologist productivity can be further evaluated by isolating these individual variables. If for example, the administrator wants to assess the impact a certain technology may have on technologist productivity, he/she can analyze and compare productivity data using the comparison technologies. If two different computed radiography (CR) devices are being analyzed, the administrator can query the database to identify productivity differences by comparing expected versus actual time differences for the two CR devices, given the same exam type. Since the PWI scores incorporate clinical, technologist, and patient-specific differences; the net impact each technology has on overall productivity can be derived. The administrator can in turn use this data to determine appropriate resource allocation including new technology purchase, staffing levels, and exam scheduling.

If on the other hand, the administrator wants to evaluate quality deliverables (e.g. report accuracy, communication of emergent findings), he/she can do so by correlating individual and collective radiologist PWI scores (with the PWI outcomes database) and QA Scorecards. If certain radiologists are identified as less prone to directly communicate emergent findings or have delayed report turnaround times, the administrator can mandate automated PWI workflow templates that incorporate these additional and/or streamlined steps to ensure timely and appropriate communication.

According to example embodiments, pooled data may be analyzed to determine a relative impact that various actions and variables may have on workflow (which may be measured e.g., by time spent) and/or quality, as measured for example by quality assurance data (e.g., off a QA scorecard—see, e.g., U.S. patent application Ser. No. 11/699,349, which is hereby incorporated by reference herein) and/or outcome data. In this scenario, the pooled information may be used for example, by a hospital, insurance company or regulatory group, etc., to help determine in which activities time is best spent, which equipment or software is most valuable, etc. with respect to obtaining a high quality workflow and/or the best outcome.

According to example embodiments, pooled data can be used for example education and training purposes, to identify optimized workflow protocols for a given set of variables and present this information at the point of contact (e.g. CT exam interpretation) to simultaneously improve workflow, technology utilization, and clinical outcomes.

A few relevant examples of an educational feedback application of PWI scores are provided below:
 1. Technologist is provided data to identify the optimized CT protocol/acquisition parameters for a given patient/clinical indication/technology (CT scanner).
 2. Radiologist is provided data to identify the optimal interpretation parameters (workstation tools, CAD, reconstruction algorithms, image processing). In addition, the automated playback capabilities of U.S. patent application Ser. No. 11/586,580, can provide a mechanism to automated workflow based on data driven "best practice" guidelines.
3. Thoracic surgeon planning for surgery can utilize the data to optimize 3-D anatomic visualization, tumor quantification, and pre-operative mapping.
4. Administrator can utilize the data to assist in data-driven technology assessment, prior to technology purchase.
5. Third party payers can utilize data to optimize financial reimbursement (both technical and professional) in accordance with workflow, quality, and clinical outcomes.

Additionally, data and/or calculated PWI scores may be subsequently available to multiple stakeholders (e.g. radiologists, technologists, administrators, researchers, clinicians, technology providers, third party payers) to assist in defining "best practice" guidelines and optimizing financial reimbursement. Thus, methods provided herein may include determining guidelines for human computer actions to be performed, using the pooled data and/or PWI scores. Methods provided herein may also be used in determining compensation guidelines for facilities and/or users, using the pooled data or PWI scores.

According to example embodiments, methods may include determining a point at which productivity gains may be offset by quality deterioration. For example, a user may be more productive as far as getting more tests done in a certain period of time if certain workflow steps are skipped or little time spent on them, but quality may suffer because key information may be missed causing e.g., missed diagnoses; further testing to be performed (which may not have been necessary), etc. By way of further example, it may be faster (more productive) for a technician to dictate a report, but errors in transcription may compromise the quality of the report and delay in transcription may also constitute a reduction in quality, particularly where time in interpreting test results is of importance. If the data and/or PWI scores are compared to quality assurance data, it may be possible to determine a point at which productivity gains are offset by quality deterioration.

By correlating the PWI and QA data (as discussed herein), one can extract a great deal of information regarding the delicate balance between maximizing productivity (i.e. speed) and quality. If for example, a radiologist is demonstrated to have deficient quality scores for a certain type of exam and certain PWI scores, then this information can be used to facilitate remedial education, request for consultations (e.g. second opinions or double reads) workflow distribution, and incorporation of automated "best practice" workflow templates. The unique ability of the PWI database to identify specific areas of PWI/QA deficiency creates a mechanism to proactively guide education based on objective need and determine the impact these proactive educational programs have on longitudinal performance measures.

One of the most important applications for the present methods, systems, etc. is the creation of a comprehensive and objective means to guide economic reimbursement. In the current system, both technical and professional reimbursement fees are the same for a given exam (e.g. chest CT), regardless of differences in technology utilized, workflow, patient/institutional profile, clinical/imaging variables, and overall outcome. The PWI database may provide an objective means to quantify these differences and create an economic reimbursement model commensurate with resource allocation, exam/patient complexity, and quality. In addition to economic reimbursement, this PWI data can also serve to objectively determine medico-legal risk and serve as an objective means to assign medical malpractice rates. Risk may also be determined based on a number of individual and collective variables including for example, the end user, patient, exam type, technology utilized, task performed, etc.)

Consumers of the service (e.g. third party payers, individual patients) can also utilize this data in order to make intelligent and data-driven decisions as to the selection of service providers. For example, PWI scores and/or comparisons may be used by a third-party payer, a patient, or a potential patient to determine the quality of a particular, physician or other healthcare or provider, in advance of having any procedures done or tests run. According to example embodiments, a patient may be able to search a database for a particular doctor, imaging center or hospital and determine how that doctor's PWI score (or outcomes or other data) compare to other doctors, hospitals or other peers that may be options for the patient. Such information if provided to the patient in advance, will allow him or her to make more informed decisions regarding their healthcare. If more and more patients are provided with this information and select the doctors/centers with higher scores, pressure will be put on doctors, providers and centers with lower scores to raise their PWI scores, which should increase quality and outcomes.

In the end, the methods, systems, apparatuses, machine-readable medium, and computer-readable program products herein provide means with which to objectively balance compensation with service deliverables.

The following examples illustrate non-limiting embodiments. The examples set forth herein are meant to be illustrative and should not in any way serve to limit the scope of the claims. As would be apparent to skilled artisans, various changes and modifications are possible and are contemplated and may be made by persons skilled in the art.

COMPARATIVE EXAMPLES

Comparative Example 1

This comparative prospective example depicts how two different radiologists may read and interpret Chest CTs very differently, which may result in different diagnoses, treatment, and/or outcome, despite being compensated the same for their interpretations, under current systems.

In this example, a patient, John Smith, has previously diagnosed lung cancer and undergoes regularly scheduled chest CT exams every 3 months to assess response to treatment. After diagnosis of the cancer, Mr. Smith underwent surgical resection of the primary cancer, followed by radiation therapy and chemotherapy. Mr. Smith sometimes has his CT exams performed at the hospital where he had surgery and other times at a nearby outpatient imaging center, located in close proximity to his oncologist's office.

A. First Radiologist

The first radiologist interpreting the chest CT at the hospital (Dr. James) is very methodical in his practice patterns. In the course of interpreting Mr. Smith's CT exam Dr. James goes through the following steps:
1. Before reviewing the current CT exam, Dr. James reviews Mr. Smith's electronic medical record (EMR) to access important historical and clinical data that may be relevant to his interpretation of the CT data. These include:
   a. Past medical history
   b. Surgical operative note
   c. Radiation and medical oncologist consultations
   d. Laboratory data
   e. Pathology report 2. In addition to the clinical data, Dr. James meticulously reviews historical and recent imaging data, including the following:
   a. Past chest CT exams (initial CT exam at the time of diagnosis (pre-treatment baseline), followed by the three post-surgical exams
   b. Reports of these CT exams
   c. Recent chest radiographic studies and corresponding reports
   d. Other relevant imaging studies (e.g. PET scan)
   e. Serial linear and volumetric tumor measurements
3. During the course of the review and interpretation process, Dr. James utilizes multiple computer workstation tools, decision support applications, and specialized image processing techniques including:
   a. Multiple window/level settings to selectively review different anatomic features and tissues within the anatomic region examined (e.g., lung, chest wall, mediastinum, vascular structures).
   b. Multi-planar reconstructions to review the data in different orthogonal planes (axial, sagital, coronal)
   c. Specialized 3-D reconstructions
   d. Linear and volumetric measurement tools
   e. Computer-aided detection software (CAD)
   f. Temporal subtraction software (to measure subtle change between successive exams)

As a result of this comprehensive and intensive interpretation process, Dr. James issues a highly detailed report that provides the referring physician with a review of the current findings, correlation with past imaging findings, and sequential tumor measurements (from the current and historical comparison exams). Along with the structured text report, Dr. James links annotated "key" electronic images that highlight pertinent findings described in the text report, along with imaging data from electronic teaching files that may be of interest to the referring clinician.

All in all, this exhaustive process takes Dr. James 15 minutes for completion. Because he utilized a computer based reporting system (GBR), he was able to generate a signed, completed report at the point of service and e-mail that report to the referring clinician immediately.

B. Second Radiologist

The second radiologist (Dr. Miller) works at the outpatient facility and also reads a chest CT on the same patient, John Smith. While Dr. Miller has similar access to Mr. Smith's EMR, he elects not to spend much time reviewing clinical and imaging data. Instead, Dr. Miller reviews and interprets the current chest CT exam and compares it only to the most recently performed chest CT study, without directly reviewing the accompanying report.

In the course of image review and interpretation, Dr. Miller reviews the CT data in a single (axial) plane and does not utilize multi-planar or 3-D reconstructions or decision support software. He dictates a report in conventional free text fashion (which is sent to a transcription service), and does not incorporate "key" images or ancillary data into the report.

By electing not to utilize clinical data, much of the past imaging data, and little of the available computer applications; Dr. Miller was far more efficient (in terms of time measurements) than Dr. James. The complete interpretation time for Dr. Miller was only 4.5 minutes. However, the report by Dr. Miller will be delayed (relative to Dr. James), because of the fact that Dr. Miller's report will require transcription prior to review and signature, whereas Dr. James was self-edited and signed at the time of interpretation.

Ironically, both radiologists may receive the same professional payment for CT interpretation, despite major differences in workflow, technology utilization, data accessed, and service deliverables. In all likelihood, the overall diagnostic accuracy of these two radiologists' reports may also differ over time, due to the marked differences in the manner in which historical and current data was reviewed and integrated into the interpretation process.

Comparative Example 2

In this comparative prospective example, two CT technologists (Sue and Barb) are working in the same medical imaging department. Both Sue and Barb will be performing chest CT scans on John Smith (from Comparative Example 1), however, the workflow for these two technologists is far different from one another.

A. First Technologist

An itemized CT workflow list for the First Technologist (Sue) as she performs Mr. Smith's CT is as follows:
1. Patient Preparation
   a. Greets the patient and explains procedure to be performed along with instructions
   b. Obtains clinical history (medical history, treatment, allergies)
   c. Obtains imaging history (outside imaging data, contrast contraindications)
   d. Inserts intravenous catheter (for contrast) and tests for proper positioning
2. Data Access and Input
   a. Review of prior CT data (images and reports from PACS, technologist data from RIS)
   b. Review of clinical data (from CPOE and EMR)
   c. Review of laboratory data (from EMR)
   d. Incorporates pertinent historical, clinical, and technical data into exam
3. Image Review
   a. Reviews acquired imaging data
   b. Repeats portions of study incomplete or of limited quality
   c. Adds additional imaging sequence/s as needed to completely visualize pathology
   d. Annotates "key" images with measurements and other data
4. Image Processing
   a. Applies pertinent image processing algorithms (in accordance to clinical indication and pathology observed)
   b. Performs 2-D and 3-D reconstructions During the course of her interaction with the patient (John Smith), Sue learns that he has had a recent allergic reaction to intravenous contrast at an outside facility. As a result, she alerts the radiologist who questions the patient further and learns that the reaction consisted of a transient episode of hives, which abated after medical therapy. As a result, the radiologist contacted the referring clinician and it was mutually decided to postpone Mr. Smith's scheduled chest CT exam with contrast until after steroid pre-medication can be administered.

Two days later, Mr. Smith returns and Sue learns (after reviewing his lab data on the EMR) that he has had a minor worsening in renal function (related to chemotherapy), which calls for a modification in the type and amount of contrast to be administered.

After inserting the intravenous catheter, Sue performs a "test run" by injecting a small volume of contrast to ensure proper working of the catheter. Due to Mr. Smith's fragile veins (related to repeated venupuncture), there is contrast leakage (extravasation) and a new catheter must be inserted. The second catheter works fine and the exam proceeds.

After completing the image acquisition, Sue independently reviews the image data prior to discharging Mr. Smith. She notices that several images are degraded by motion artifact (due to respirations) and she repeats that portion of the exam degraded by motion. She also notices that the inferior-most image (within the upper abdomen) demonstrated an abnormality of the left adrenal gland, so she acquires additional images inferiorly until she has imaged the questionably abnormal left adrenal gland in its entirety.

In the course of her image processing, Sue performs multi-reconstructions for the radiologist along with linear and density measurements of the enlarged left adrenal gland. All reconstructed and annotated images are saved in the CT data filed (along with the primary dataset) and stored in the PACS archive for future review and reference. The additional data acquired (with regards to the enlarged left adrenal gland) prompted the radiologist to diagnose a metastasis (based on density, size, and morphology); which changed Mr. Smith's clinical treatment.

B. Second Technologist

The second technologist, Barb, (like Dr. Miller of Comparative Example 1) is not as compulsive or methodical as Sue. Her "patient preparation" is not as detailed and she does not make detailed inquiries as to past imaging studies or complications. As a result, Sue does not learn of Mr. Smith's past allergic reaction, and proceeds by preparing to administer the full contrast dose. Barb does not perform an independent "test dose" to assess catheter positioning. As a result, there is immediate contrast extravasation (which is quickly recognized after 30 cc of the expected 120 cc are administered). The small volume of contrast administered does not produce an allergic reaction or significant tissue injury. It does however preclude post-contrast imaging, which limits the amount of diagnostic information contained on the CT dataset (as opposed to that contained on a post-contrast CT dataset). The small volume of contrast administered (due to extravasation) has the additional advantage of reducing any potential contrast-induced nephrotoxicity (due to chemotherapy-impaired renal function). Because barb did not take the time to review Mr. Smith's EMR lab data (BUN, creatinine), unlike Sue, she was unaware of this critical data.

Once the imaging data has been acquired, Barb discharges Mr. Smith without a detailed review of the CT dataset. The resultant motion artifact goes unnoticed, as does the questionable abnormality in the incompletely visualized left adrenal gland. Barb submits the "completed" CT dataset to the PACS for radiologist interpretation, without additional annotations, measurements, or reconstructions. As a result of the exam limitations, the radiologist interpreting the CT data did not identify the adrenal metastasis, which was eventually diagnosed several months later on a follow-up CT exam.

From a productivity standpoint, Barb is more "efficient" than Sue because her "total exam time" was only 12 minutes, compared to Sue's "total exam time" of 21 minutes. Several of the additional steps performed by Sue account for these time differences and clearly had a significantly positive impact on patient care, radiologist satisfaction, and clinical outcomes. Unfortunately, the existing RVU system does not quantify the workflow differences and provides a single productivity score independent of image quality, informational detail, and technology utilized.

Comparative Example 3

This comparative prospective example depicts how two different cardiologists may perform consultations very differently, one resulting in a timely and accurate diagnosis, when compared with the more abbreviated consultation performed by the other, which resulted in delayed diagnosis and treatment.

During the course of his treatment (chemotherapy), Mr. Smith is experienced chest pain, prompting his oncologist to request a cardiology consultation.

A. First Cardiologist

In this example, the consulting cardiologist (Dr. Edwards) performs the consultation after a careful review of the following information contained within the EMR:
1. History and Treatment of Current Illness (Lung cancer)
2. Past Medical History (hypertension)
3. Laboratory Data (cardiac enzymes)
4. Imaging Data (Chest CT)
5. Clinical Testing (EKG)

Dr. Edwards proceeds to perform a detailed history and physical exam of the patient. After correlating the historical, clinical, and physical data Dr. Edwards is suspecting chemotherapy-induced cardiomyopathy as the underlying etiology. He consults the pharmacist about the specific medication and chemotherapeutic regimen Mr. Smith is on and suspects one of the chemotherapy agents (which is new and in clinical trials) may be the offending agent. Dr. Edwards performs a computerized literature search using the National Library of Medicine and finds that there have been a few case reports of this particular drug producing cardiomyopathy in patients with a similar clinical profile to Mr. Smith.

To confirm his suspicion, Dr. Edwards orders a stress echocardiography exam, which confirms the diagnosis in question. The chemotherapy regimen is altered (removing the drug in question) and Mr. Smith's clinical status improves within a few days.

B. Second Cardiologist

A second cardiologist (Dr. Fast) is making weekend rounds for the same cardiology group that Dr. Edwards works for. Not knowing that Dr. Edwards had previously consulted on Mr. Smith, he inadvertently performs the consultation requested by the referring oncologist. Dr. Fast obtains history directly from Mr. Smith followed by a bedside physical exam and a cursory review of the EMR. Based on his experience with similar patients (longstanding smoking, hypertension, and lung cancer), he determines the chest pain is the result of angina and prescribes a corresponding drug regimen (in addition to Mr. Smith's ongoing chemotherapy regimen). When Mr. Smith has another bout of chest pain the next day (Sunday), Dr. Fast orders an emergent cardiac catheterization which is determined to be normal.

In this scenario, the cardiology consultations performed by both cardiologists resulted in the same reimbursement, despite marked differences in workflow and time. The more time-consuming consultation performed by Dr. Edwards resulted in a more timely and accurate diagnosis, when compared with the more abbreviated consultation performed by Dr. Fast, which resulted in an unnecessary and costly procedure (cardiac catheterization) and delayed diagnosis and treatment.

EXAMPLES

Example 1

This is a non-limiting example method in which PWI scores may be calculated.

The ability to create structured (standardized) data elements within the various PWI profiles provides a mechanism to perform statistical analysis over large populations of end-users. This has the additional advantage of selectively performing analyses on comparable peer groups, ensuring that the reference statistics are applicable to a number of variables (e.g. technology utilized and institutional profile).

The calculation of comprehensive or pooled PWI score represents a compilation (summation) of individual PWI profile scores (and their various components), and includes for example, patient, institutional, clinical, imaging, technology, exam, and outcome profiles. A differential weighting can be applied to each individual profile depending upon the perceived importance of that specific profile in determining the complexity and challenge of the task to be performed. (The weighting may be periodically reassessed and/or refined based on various factors, such as reassessment of the data, reassessment of relative importance of various factors, etc.)

For the purposes of illustration, a differential weighting is assigned to the profiles presented herein (which are also non-limiting examples) for the representative task of radiologist CT interpretation. The following is an example differential weighting of profile data for comprehensive PWI score calculation

| | | |
|---|---|---|
| 1. | Patient profile (measure of patient compliance) | 5% |
| 2. | Institutional profile (measure of operational efficiency) | 5% |
| 3. | Clinical profile (measure of disease-specific complexity) | 20% |
| 4. | Imaging profile (measure of complexity and volume of historical imaging data) | 20% |
| 5. | Technology profile (measure of supporting technology efficiency) | 10% |
| 6. | Exam profile (measure of size/complexity of dataset and tools used for analysis) | 20% |
| 7. | Outcomes profile (measure of quality indicators and clinical outcome) | 20% |

Example 2

The following is a non-limiting example of how data may be stored and derived, and how a PWI score may be calculated in accordance with non-limiting embodiments.

A computer can automatically access or derive the following data (for example, by referencing various databases, such as the PWI, Quality Assurance, Snapshot and/or workflow databases):

1. PWI values associated with each individual application.
2. Collective PWI values associated with the collective workflow steps performed.
3. Individual and collective time requirements associated with individual applications and PWI values.
4. Differential PWI values associated with different technologies and applications offered.
5. Comparison PWI and time measures associated with comparative workflow templates.

A non-limiting representative example of how PWI and associated data may be computed is presented below.

1. A radiologist (Dr. Hanson) opens the exam to be interpreted, which may be a chest (thoracic) CT on patient Henry Jones.
2. The radiologist selects the "manual" mode of operation, thereby electing to navigate through the imaging dataset and invoke the various toolsets and software applications independently.
3. Once the manual workflow option is begun all subsequent computer actions are electronically recorded (e.g., using Snapshot as discussed in U.S. patent application Ser. No. 11/586,580) in an XML schema that is simultaneously entered into workflow and PWI databases.
4. The radiologist begins by reviewing the ordering data (which was entered into the CPOE) that states the clinical indication and past medical history. This step is recorded and analyzed by the PWI database, which assigns a PWI value of 6 points and a time value of 15 seconds.
5. The radiologist subsequently opens up the patient's clinical folder in the EMR) and reviews the recent hospital admission history and physical (H & P), pulmonologist consultation note, and bronchoscopy report. The PWI database assigns a collective PWI value of 40 points and a time value of 2 minutes 15 seconds.
6. Dr. Hanson opens up the patient's imaging folder in the PACS and identifies several prior imaging studies of the thorax on this patient, including 4 serial chest radiographs and 2 prior chest CT examinations. He elects to review the corresponding reports on the most recent chest radiograph (CXR) and chest CT, with respectively assigned PWI values of 6 points for the CXR report and 18 points for the CT report.
7. Dr. Hanson elects to open up the prior chest CT exam and review selected "key" images with pathologic findings, which have been annotated and stored in a separate sub-folder from the main study. The entire sub-folder contains 16 images, but Dr. Hanson only directly views 8 images (all in the axial plane). Based on the recorded time and workstation tool usage in reviewing these images, a PWI value of 15 points is assigned, base on the tracked workflow time of 40 seconds.
8. Dr. Hanson proceeds to display and review the current imaging folder, consisting of 425 total images. During the navigation of the dataset, all 425 images are reviewed in the axial plane along with reconstructed images in the coronal plane. The PWI assigns a value of 80 points for the axial imaging plane review and an additional value of 16 points for reconstruction and review in the orthogonal coronal plane. Based on the data retrieved from the PWI and workflow databases, a corresponding time value of 6 minutes is assigned, which in actuality differs from the observed time measurement of 7 minutes 12 seconds.
9. During the course of image navigation and review, the electronic auditing tool records utilization of the following workstation tool functions:
    a. Manual window/level adjustment.
    b. Linear and volumetric measurements of a lung nodule in the left lung.
    c. Comparison linear measurements of the same nodule from the prior chest CT exam.
    d. Review of imaging dataset using 4 different automated window/level presets.
    e. Activation of the computer aided detection (CAD) software program for lung nodule detection.
10. Based on the recording of these workflow steps, the PWI database assigns an additional value of 35 points and 80 seconds.
11. During the creation of the report, Dr. Hanson creates 6 "key" images of pathologic findings, which are manually annotated by him, stored in a sub-folder, and electronically attached to the text report. The creation of these annotated images is assigned an additional 40 points and time value of 2 minutes and 15 seconds.

12. After completing the report, Dr. Hanson consults the referring clinician via telephone, and documents this communication in the report. This communication is recorded in the workflow and PWI databases and is assigned values of 25 points and 1 minute 30 seconds.
13. The PWI database presents the observed and expected cumulative totals to Dr. Hanson as follows:
Actual PWI value: 281 points
Expected PWI values (from comprehensive PWI database): mean 225 points,
range: 165-310 points
Actual interpretation time: 12 minutes 27 seconds
Expected interpretation times (from workflow and PWI databases): mean 8 minutes 45 seconds, range: 6 minutes 15 seconds-14 minutes 45 seconds Example 3

According to non-limiting example embodiments, using automated analysis of the PWI databases and data contained within information system technologies (e.g. CPOE, RIS, PACS, EMR) pertaining to the specific task at hand, an automated PWI score may be presented before an end-user begins the task at hand. This automated PWI score may be based for example, on historical data specific to the task (from the reference population group) and the individual end-user's profile. This Pre-task PWI score can serve to provide the end-user with reference values of the anticipated task complexity and time requirements. In addition, the end-user can request for reference PWI scores to be presented which provide comparable PWI scores for other end-users performing the same task (e.g. colleagues within the same radiology department or a local institution).

In the event that the end-user wants to adjust the PWI score in either an upward (i.e. greater complexity and time requirements) or downward fashion (i.e. less complexity and time requirements), he/she can manually adjust the predicted PWI score in the corresponding direction and the computer can present variables which can be modified to reflect the requested change. As an example, a radiologist who desires to decrease the predicted PWI score on a chest CT (performed for lung cancer screening) can be presented with a number of workflow variables (e.g. decreased number of window/level settings reviewed, image review in a single axial lane only) which if utilized will produce a net decrease in the PWI score. The radiologist can elect to exercise these optional changes in workflow by invoking the "automated workflow" mode, which will incorporate these modifications into the computer-generated workflow. Any change from the "automated workflow" mode (produced by radiologist-generated commands) will automatically adjust the PWI score commensurate with the modifications performed and corresponding time changes. After completion of the task, the "actual" PWI score (as opposed to the "predicted" PWI score) will be recorded and available for review. These "predicted" and "actual" PWI scores are recorded and stored within the PWI database for future review and analysis.

The "actual" PWI score, which is calculated at the end of task completion, is not truly a "final" PWI score, because the longitudinal outcomes analysis has not taken place. The outcome profile score, which is utilized for the initial PWI score, is a compilation of historical outcomes analysis of the individual end-user and the specific task performed (based on historical analysis of "comparable" end-users). This outcome analysis data can also be correlated from data contained within the QA Scorecards (separate invention), which tracks a number of quality-centric variables, which contribute to outcomes and overall quality measures.

If PWI and QA Scorecard (see e.g., U.S. patent application Ser. No. 11/699,349) databases are integrated with one another, assessment of exam quality can be automatically calculated and incorporated into the Exam profile score. If this is not available, subjective image quality assessment can be performed by the radiologist (for example) at the time of interpretation. This data may be an important determinant of the performing technologist's PWI score.

Example 4

Figure 4:
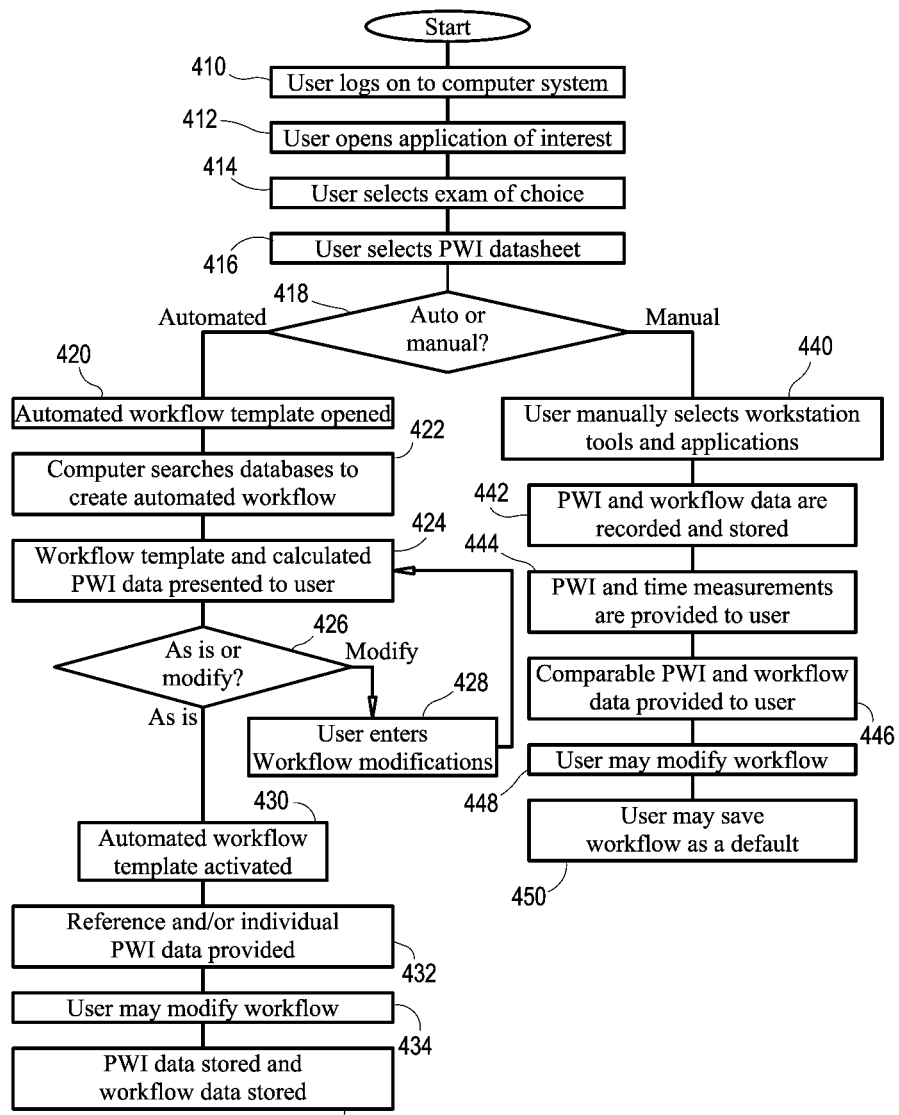
FIG. 4 is a detailed flowchart of an example method in accordance with non-limiting example embodiments.

This is a non-limiting detailed example of some of the methods provided herein. In particular, this example is a detailed illustration of how software may be used to guide a user's workflow and determine an individual's PWI score. This representative prospective example is for a radiologist interpretation of an imaging study, but the present methods are not limited to radiologists or to imaging studies.
1. End-user logs onto computer system 410 (see FIG. 4) (Biometrics).
2. End-user opens up specific application of interest 412 (e.g. Unread CT exams).
3. User selects exam of choice 414 (e.g. Chest CT, John Smith).
4. User selects PWI datasheet 416, which contains a number of individual profiles, each of which contains a number of individual variables, including for example one or more of the following:
   a. Patient profile (patient demographic data).
   b. Institutional profile (institutional demographic data).
   c. Clinical profile (patient-specific laboratory, pathology, and genetic data; past medical/surgical historical data).
   d. Examination profile (acquisition, processing, and quality data intrinsic to the imaging dataset).
   e. Technology profile (information and decision support technologies available).
   f. Outcome analysis profile (clinical outcomes data).
5. End-user may have an option of selecting "Automated" or "Manual" modes of operation 418.
A. Automated Mode:
6a. Computer opens up user and context-specific profiles to create automated workflow template 420.
   User-specific profile: contains individual user's priority order of variables to use.
   Context-specific profile: Priority order of parameters specific to that particular exam type and clinical indication.
7a. Computer searches PWI and/or other databases such as a database created according to U.S. patent application Ser. No. 11/586,580, to identify/create corresponding automated workflow template 422.
8a. Itemized workflow template and calculated PWI data (based on automated workflow template) are presented to end-user 424.
9a. End-user selects option to select "as is" or "modify" 426.
10a. If "modify" function is selected, end-user enters desired workflow modifications (from either workflow pick-list or manual input) 428.
11a. Updated PWI data presented to end-user (based on revised workflow).
12a. User selects "as is" and automated workflow template is activated 430.

13a. At any time during workflow, end-user can start, stop, or manually revise automated workflow template.
14a. All workflow steps may be recorded in XML schema and entered into PWI and workflow databases.
15a. At the conclusion of operation, revised PWI data is presented to the end-user along with reference PWI data from other users of similar exam types and clinical indications (i.e., pooled data of at least one other peer group) 432.
16a. End-user can review comparison workflow templates (and corresponding PWI data) by activating "reference data" application.
17a. End-user can edit his/her user-specific workflow profile by simply adding/subtracting workflow steps from his/her user-specific workflow profile, or select one of the reference workflow templates 434.
18a. Any modifications made to the workflow templates will have corresponding PWI data presented which incorporates changes in PWI values and estimated workflow time requirements.
19a. As each new application is opened, PWI and workflow data are recorded and stored in corresponding databases 436.
20a. Using the Outcomes profile, end-user can select a desired clinical outcome (e.g. diagnostic accuracy) and query the computer to provide an automated workflow template used by end-users with the highest measures of that specific outcome (diagnostic accuracy).
21a. End-user can request future automated workflow templates use default templates of those end-users with highest outcome measures in the category of highest priority.

B. Manual Mode:

6b. End-user manually selects individual workstation tools and applications desired 440.
7b. As each new application is opened, PWI and workflow data are recorded and stored in corresponding databases 442.
8b. As workflow continues, updated PWI and time measurements are provided to the end-user 444.
9b. At the time of exam completion, end-user is presented with comparable PWI and workflow data from other end-users as reference 446.
10b. If end-user desires to view other workflow options and corresponding PWI data, he/she can click on the specific workflow step of interest and the computer will present corresponding PWI and time data associated with that application. The user may modify the workflow 448.
11b. After completion of the process, end-user can select "automated default" option to incorporate the workflow used into a new automated workflow template for that specific exam type and clinical profile. Thus, the user may essentially save a workflow system that is either created by scratch by the user, or it may have been an automatic workflow system that the user has slightly modified 450.

In an automated mode, end-users may use workflow templates to effectively review the imaging data in a "hands off" manner. In a manual mode, end users may use the workflow XML schema to automatically drive workflow. According to example embodiments, end-users may switch between navigating through workflow systems in an "automatic" and "manual" manner. Manual navigation may include performing end-user driven tasks. A user may return to "automatic" workflow navigation mode to re-engage the automatic workflow template navigation and continue e.g., from a selected point within a workflow template navigation sequence.

It should be understood that various of the above steps may be modified or omitted in accordance with the present invention, and may be performed in a different order than presented in this example.

Example 5

Figure 5:
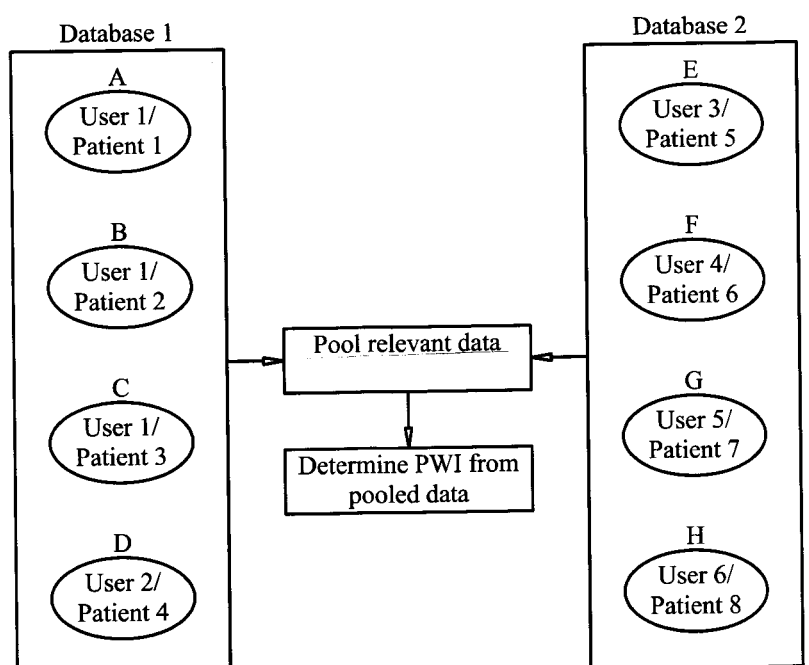
FIG. 5 demonstrates examples of how various subsets of data may be pooled to calculate specific desired PWI values in accordance with non-limiting example embodiments.

FIG. 5 depicts examples of various data sets (A-H) that may be obtained from one or more databases and pooled together in accordance with non-limiting example embodiments.

As depicted in FIG. 5, data sets A-C are recorded data for human computer actions and workflow variables relating to a first user, but with respect to a first patient (dataset A), a second patient (dataset B), and a third patient (dataset C). Dataset D relates to a second user/fourth patient, dataset E relates to a third user/fifth patient, dataset F relates to a fourth user/sixth patient, dataset G relates to a fifth user/seventh patient, and dataset H relates to a sixth user/eighth patient. Some of the demographic information regarding set of data are provided in Table 1 below.

TABLE 1

| Dataset | Database in which data is stored | User | Patient | User Profession | Facility | Location | |
|---|---|---|---|---|---|---|---|
| A | 1 | 1 | 1 | Radiologist | Hospital X | Midatlantic | Urban |
| B | 1 | 1 | 2 | Radiologist | Hospital X | Midatlantic | Urban |
| C | 1 | 1 | 3 | Radiologist | Hospital X | Midatlantic | Urban |
| D | 1 | 2 | 4 | Radiologist | Hospital Y | West Coast | Urban |
| E | 2 | 3 | 5 | Radiologist | Hospital Y | West Coast | Urban |
| F | 2 | 4 | 6 | Technician | Imaging Center W | Midatlantic | Rural |
| G | 2 | 5 | 7 | Radiologist | Hospital Z | Mid-west | Rural |
| H | 2 | 6 | 8 | Technician | Hospital X | Midatlantic | Urban |

According to example methods provided herein, pooled PWI scores may be determined from various subsets of data depending on the information sought and may be from one or more databases. Non-limiting example embodiments of possible pooled PWI scores that may be calculated in the present example are as follows: A PWI score may be determined for User 1 overall, by analyzing the data from Datasets A, B, and C. A PWI score may be determined for all radiologists by analyzing pooled data from Datasets A, B, C, D, E and G. A PWI score may be determined for all users in Hospital X by analyzing pooled data from Datasets A, B, C, and H. A PWI score may be determined for all users in the Midatlantic region by analyzing pooled data from Datasets A, B, C, F, and H. A PWI score may be determined for all users in rural areas by analyzing pooled data from Datasets F and G.

Further, to even more narrowly define a search, for example when a comparison to a specific review group or peer group is desired, data may be selected using multiple criteria. For example, a PWI score may be determined for all radiologists in the Midatlantic region by analyzing pooled data from Datasets A, B, and C. A PWI score may be determined for all technicians in the Midatlantic region by analyzing pooled data from Datasets F and H.

Although the inventions have been described in example embodiments, many additional modifications and variations would be apparent to those skilled in the art. For example, modifications may be made for example to the methods described herein including the addition of or changing the order of various steps. Modifications may be made to the example analyses provided herein. Other examples of possible modifications may include modifications to the PWI output. Further modifications may be made to the overall methods, systems, etc. where a Productivity Workflow Index may be calculated for example to non-medical scenarios, e.g., where the "patient" is not necessarily a medical patient, but is a customer or other person or entity. It is therefore to be understood that this invention may be practiced other than as specifically described. Thus, the present embodiments should be considered in all respects as illustrative and not restrictive.

What is claimed is:

1. A computer-implemented method for determining productivity in medical workflow processes comprising
recording human-computer actions by a first user relating to a first patient in a database of a computer system, said human-computer actions including at least user-performed workflow activities and time spent on each of said activities, said user being a medical professional;
recording workflow related variables related to at least said first patient, said medical professional, and clinical and examination variables, in said database;
recording data regarding the human-computer actions and the workflow related variables to said database;
repeating the recording steps multiple times for a second or more users, said second or more users being medical professionals, relating to a second or more patients;
pooling said data on said users for analysis; and
determining at least one Productivity Workflow Index score from the pooled data, said Productivity Workflow Index score which is calculated based upon a weighting system of individual data elements including said human-computer actions, and said time spent on each said human-computer actions, said data elements which are assigned a numerical value, to assess productivity of said users; and
wherein said Productivity Workflow Index score is used to compare said users to one another for purposes of determining said productivity of said users; and
determining in real-time whether there is additional information to be included, or additional tasks to be performed, in said human computer actions, based upon an analysis of Productivity Workflow Index scores from said pooled data, in order to improve said productivity of said users.

2. The method of claim 1, wherein the recording includes time-stamping the human-computer actions.

3. The method of claim 1, wherein the workflow-related variables include at least one a patient profile, an institutional profile, a technology profile, a clinical profile, an imaging profile, an exam profile, and an outcomes profile.

4. The method of claim 1, wherein the Productivity Workflow Index score is based on pooled data from at least one group of data selected from one of a common profession of users, a common facility of users, a common geographic location of users, and common resources of users.

5. The method of claim 1, further comprising:
analyzing said pooled data to determine a relative impact said workflow-related variables and said human-computer actions have on workflow and/or quality.

6. The method of claim 1, further comprising:
determining a point at which productivity gains are offset by quality deterioration by comparing at least one Productivity Workflow Index score to quality assurance data.

7. The method of claim 1, further comprising:
determining guidelines for human-computer actions to be performed, using the pooled data.

8. The method of claim 1, further comprising:
determining compensation guidelines, using the pooled data.

9. The method of claim 1, wherein the Productivity Workflow Index score is determined by weighting individual data elements.

10. The method of claim 1, further comprising:
determining a Productivity Workflow Index score for a single user or multiple users based on that user's human-computer actions and workflow-related variables; and
comparing the Productivity Workflow Index score for each of said users, to at least one Productivity Workflow Index from the pooled data.

11. The method of claim 10, wherein the Productivity Workflow Index score for the single user is determined based on data regarding one or more patients.

12. The method of claim 10, wherein the pooled data is one of pooled data from users at the same facility as the single user; pooled data from a common profession of users as the single user, pooled data from a common geographic location of users as the single user, and pooled data from users having common resources as the single user.

13. The method of claim 1, further comprising,
determining a Productivity Workflow Index score for a first pooled group of users and patients based on human-computer actions and workflow-related variables within the pooled group; and
comparing the Productivity Workflow Index score for the first pooled group, to at least one Productivity Workflow Index from a second pooled group of users and patients.

14. The method of claim 1, further comprising:
issuing an electronic alert to said users when a specific human computer action was not performed.

15. The method of claim 1, further comprising:
providing an estimated completion time for users performing human-computer actions in such that said users can pace their actions.

16. The method of claim 15, further comprising:
issuing an automated alert when a user exceeds expected measures at predetermined time periods.

17. An apparatus which determines productivity in a medical workflow, comprising:
a memory containing at least one program having the steps of:
recording human-computer actions by a first user relating to a first patient in a database of a computer system, said human-computer actions including at least user-performed workflow activities and time spent on each of said activities, said user being a medical professional;

recording workflow related variables related to at least said first patient, said medical professional, and clinical and examination variables, in said database;
recording data regarding the human-computer actions and the workflow related variables to said database;
repeating the recording steps multiple times for a second or more users, said second or more users being medical professionals, relating to a second or more patients;
pooling said data on said users for analysis; and
determining at least one Productivity Workflow Index score from the pooled data, said Productivity Workflow Index score which is calculated based upon a weighting system of individual data elements including said human-computer actions, and said time spent on each said human-computer actions, said data elements which are assigned a numerical value, to assess productivity of said users; and
wherein said Productivity Workflow Index score is used to compare said users to one another for purposes of determining said productivity of said users; and
determining in real-time whether there is additional information to be included, or additional tasks to be performed, in said human computer actions, based upon an analysis of Productivity Workflow Index scores from said pooled data, in order to improve said productivity of said users; and
a processor for executing the program.

18. A non-transitory machine-readable medium comprising
code segments embodied on a medium that, when read by a machine, cause the machine to perform the steps of:
recording human-computer actions by a first user relating to a first patient in a database of a computer system, said human-computer actions including at least user-performed workflow activities and time spent on each of said activities, said user being a medical professional;
recording workflow related variables related to at least said first patient, said medical professional, and clinical and examination variables, in said database;
recording data regarding the human-computer actions and the workflow related variables to said database;
repeating the recording steps multiple times for a second or more users, said second or more users being medical professionals, relating to a second or more patients;
pooling said data on said users for analysis; and
determining at least one Productivity Workflow Index score from the pooled data, said Productivity Workflow Index score which is calculated based upon a weighting system of individual data elements including said human-computer actions, and said time spent on each said human-computer actions, said data elements which are assigned a numerical value, to assess productivity of said users; and
wherein said Productivity Workflow Index score is used to compare said users to one another for purposes of determining said productivity of said users; and
determining in real-time whether there is additional information to be included, or additional tasks to be performed, in said human computer actions, based upon an analysis of Productivity Workflow Index scores from said pooled data, in order to improve said productivity of said users.

19. A non-transitory computer-readable medium comprising a program having the steps of:
recording human-computer actions by a first user relating to a first patient in a database of a computer system, said human-computer actions including at least user-performed workflow activities and time spent on each of said activities, said user being a medical professional;
recording workflow related variables related to at least said first patient, said medical professional, and clinical and examination variables, in said database;
recording data regarding the human computer actions and the workflow related variables to said database;
repeating the recording steps multiple times for a second or more users, said second or more users being medical professionals, relating to a second or more patients;
pooling said data on said users for analysis; and
determining at least one Productivity Workflow Index score; from the pooled data, said Productivity Workflow Index score which is calculated based upon a weighting system of individual data elements including said human-computer actions, and said time spent on each said human-computer actions, said data elements which are assigned a numerical value, to assess productivity of said users; and
wherein said Productivity Workflow Index score is used to compare said users to one another for purposes of determining said productivity of said users; and
determining in real-time whether there is additional information to be included, or additional tasks to be performed, in said human computer actions, based upon an analysis of Productivity Workflow Index scores from said pooled data, in order to improve said productivity of said users.

20. A computer-implemented method for determining productivity in a radiology workflow process comprising
recording human-computer actions by a first user relating to a first patient in a database of a computer system, said human-computer actions including at least user-performed workflow activities and time spent on each of said activities, said user being a radiologist;
recording workflow related variables related to at least said first patient, said radiologist, and clinical and examination variables, in said database;
recording data regarding the human-computer actions and the workflow related variables to said database;
repeating the recording steps multiple times for a second or more users, said second or more users being radiologists, relating to a second or more patients;
pooling said data on said users for analysis; and
determining at least one Productivity Workflow Index score from the pooled data, said Productivity Workflow Index score which is calculated based upon a weighting system of individual data elements including said human-computer actions, and said time spent on each said human-computer actions, said data elements which are assigned a numerical value, to assess productivity of said users; and
wherein said Productivity Workflow Index score is used to compare said users to one another for purposes of determining said productivity of said users; and
determining in real-time whether there is additional information to be included, or additional tasks to be performed, in said human computer actions, based upon an analysis of Productivity Workflow Index scores from said pooled data, in order to improve said productivity of said users.

* * * * *